(12) United States Patent
Green et al.

(10) Patent No.: US 9,381,189 B2
(45) Date of Patent: Jul. 5, 2016

(54) INGREDIENTS FOR INHALATION AND METHODS FOR MAKING THE SAME

(75) Inventors: Matthew Michael James Green, Wiltshire (GB); Richard Michael Poole, Wiltshire (GB)

(73) Assignee: VECTURA LIMITED, Wiltshire (GB)

( * ) Notice: Subject to any disclaimer, the term of this patent is extended or adjusted under 35 U.S.C. 154(b) by 641 days.

(21) Appl. No.: 13/514,672

(22) PCT Filed: Dec. 8, 2010

(86) PCT No.: PCT/GB2010/052053
§ 371 (c)(1),
(2), (4) Date: Aug. 20, 2012

(87) PCT Pub. No.: WO2011/070361
PCT Pub. Date: Jun. 16, 2011

(65) Prior Publication Data
US 2012/0309809 A1    Dec. 6, 2012

(30) Foreign Application Priority Data

Dec. 8, 2009  (GB) .................................. 0921481.8

(51) Int. Cl.
| | | |
|---|---|---|
| *A61K 9/14* | (2006.01) | |
| *A61K 31/404* | (2006.01) | |
| *B02C 23/00* | (2006.01) | |
| *C07D 209/16* | (2006.01) | |
| *A61K 31/4045* | (2006.01) | |
| *A61K 9/00* | (2006.01) | |

(52) U.S. Cl.
CPC .............. *A61K 31/4045* (2013.01); *A61K 9/141* (2013.01); *A61K 9/0073* (2013.01)

(58) Field of Classification Search
None
See application file for complete search history.

(56) References Cited

U.S. PATENT DOCUMENTS

| | | | | |
|---|---|---|---|---|
| 4,582,265 | A  * | 4/1986 | Petronelli | ........................ 241/95 |
| 6,257,233 | B1 | 7/2001 | Burr et al. | |
| 2004/0118007 | A1 * | 6/2004 | Chickering et al. | ............. 34/360 |
| 2006/0257491 | A1 * | 11/2006 | Morton et al. | ................. 424/489 |
| 2008/0063719 | A1 * | 3/2008 | Morton et al. | ................. 424/489 |

FOREIGN PATENT DOCUMENTS

| | | | |
|---|---|---|---|
| EP | 0709086 | A2 | 5/1996 |
| EP | 1498116 | A1 | 1/2005 |
| GB | 2387781 | A | 10/2003 |
| JP | 2005298347 | | 10/2005 |
| JP | 2009541393 | | 11/2009 |
| JP | 2012542618 | | 6/2012 |
| WO | 9623485 | A1 | 8/1996 |
| WO | 9703649 | A1 | 2/1997 |
| WO | 0200197 | A1 | 1/2002 |
| WO | 0243701 | A2 | 6/2002 |
| WO | 2005105043 | A2 | 11/2005 |
| WO | 2007053904 | A1 | 5/2007 |
| WO | 2008000482 | | 1/2008 |
| WO | 2009095684 | A1 | 8/2009 |

OTHER PUBLICATIONS

Brunauer et al. "Adsorption of Gases in Multimolecular Layers", J. Am. Chem. Soc., vol. 60, (Feb. 1938) pp. 309-319.
Nagai, et al. "Improvement in Dissolution Property of Poorly Water-Soluble Drugs by Using Mechanofusion System." J. Soc. Powder Technol., Japan, 43, 640-647 (2006).
Japanese Pharmaceutical Additives Directory 2007, p. 138.

* cited by examiner

*Primary Examiner* — Bethany Barham
*Assistant Examiner* — Melissa Javier
(74) *Attorney, Agent, or Firm* — Matthew S. Gibson; Reed Smith LLP

(57) ABSTRACT

A method of processing an active ingredient, the method comprising submitting a pharmaceutically active ingredient in the absence of excipients and/or additives to compression and shearing forces. The invention also relates to compositions comprising an active prepared by the method.

16 Claims, 5 Drawing Sheets

Fig 5

Figure 1:
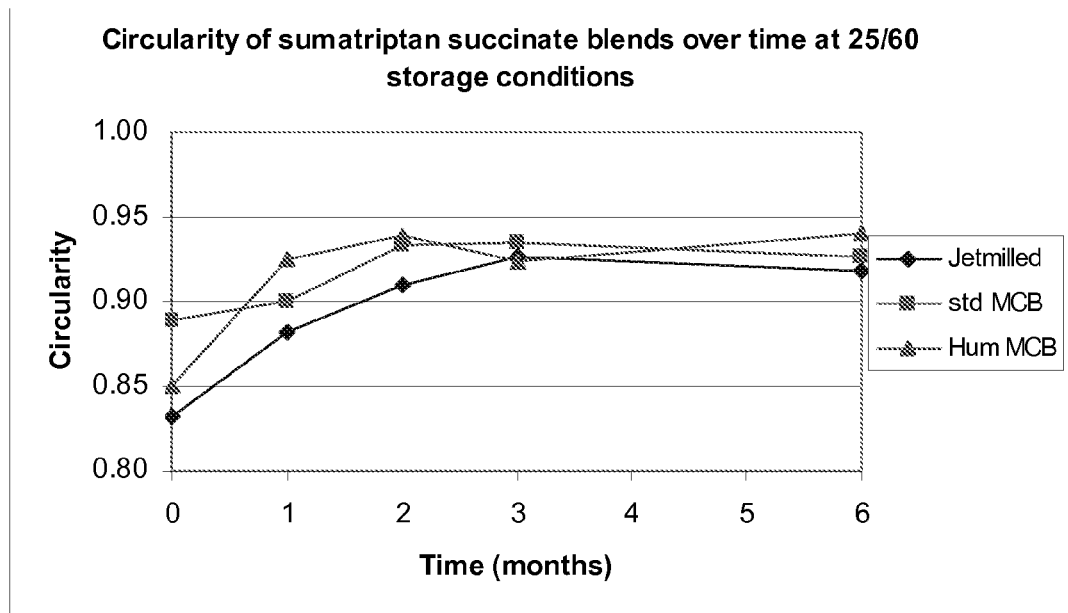

CE d(50) of sumatriptan succinate blends over time at 25/60 storage conditions

— Jetmilled
— std mcb
— Hum MCB

Fig 6

CE d(50) of sumatriptan succinate blends over time at 40/75 storage conditions

— Jetmilled
— std mcb
— Hum MCB

INGREDIENTS FOR INHALATION AND METHODS FOR MAKING THE SAME

RELATED APPLICATIONS

This application is the United States National Stage Application of International Application No. PCT/GB2010/052053, filed Dec. 8, 2010, which was published as International Publication No, WO 2011/070361 A1, and which claims benefit of Great Britain Patent Application No. 0921481.8 filed Dec. 8, 2009. Both applications are incorporated by reference in their entirety herewith.

The present invention relates to active ingredients for inhalation and methods for making such active ingredients.

Inhalation represents a very attractive, rapid and patient-friendly route for the delivery of systemically acting drugs, as well as for drugs that are designed to act locally on the lungs themselves. It is particularly desirable and advantageous to develop technologies for delivering drugs to the lungs in a predictable and reproducible manner.

The key features which make inhalation a useful drug delivery route are: rapid speed of onset; improved patient acceptance and compliance for a non-invasive systemic route; reduction of side effects; product life cycle extension; improved consistency of delivery; access to new forms of therapy, including higher doses, greater efficiency and accuracy of targeting; and direct targeting of the site of action for locally administered drugs, such as those used to treat lung diseases.

However, the powder technology behind successful dry powders and dry powder inhaler (DPI) or pressured metered dose inhalers (pMDI) products remains a significant technical hurdle to those wishing to succeed with this route of administration and to exploit the significant product opportunities. Any formulation suitably has properties that allow for the manufacture and metering of the powders, provide reliable and predictable resuspension and fluidisation, and avoid excessive retention of the powder within the dispensing device.

A major problem experienced by formulators is the variability in surface properties of drug particles. Each active agent powder has its own unique inherent stickiness or surface energy, which can range tremendously from compound to compound. Further, the nature of the surface energies can change for a given compound depending upon how it is processed. For example, jet milling is notorious for generating significant variations in surface properties because of the aggressive nature of the collisions it employs. Such variations can lead to increased surface energy, increased cohesiveness, adhesiveness and process induced disorder.

In order to improve the properties of powder formulations, and in particular to improve the flowability and dispersibility of the formulation, dry powder formulations can include additive materials which are intended to reduce the cohesion between the fine particles in the dry powder formulation. It is thought that the additive material interferes with the bonding forces between the small particles, helping to keep the particles separated and reducing the adhesion and cohesion of such particles to one another, to other particles in the formulation if present and to the internal surfaces of the inhaler device. Where agglomerates of particles are formed, the addition of particles of additive material decreases the stability of those agglomerates so that they are more likely to break up in the turbulent air stream created on actuation of the inhaler device, whereupon the particles are expelled from the device and inhaled.

The reduced tendency of the particles to bond strongly, either to each other or to the device itself, not only reduces powder cohesion and adhesion, but can also promote better flow characteristics. These effects lead to improvements in the dose reproducibility because it reduces the variation in the amount of powder metered out for each dose and improves the release of the powder from the device. It also increases the likelihood that the active material which does leave the device will reach the lower lung of the patient.

The use of additive materials in this manner is disclosed in WO 96/23485 and WO 97/03649.

It is also known that intensive co-milling of micronised drug particles with additive material may be carried out in order to produce composite active particles. This co-micronisation can improve dispersibility, as disclosed in WO 02/43701. In addition, WO 02/00197 discloses the intensive co-milling of fine particles of excipient material with additive material, to create composite excipient particles to which fine active particles and, optionally, coarse carrier particles may be added. This co-micronisation of fine excipient particles and additive material has also been shown to improve dispersibility.

There is still a need for improved dry powder formulations.

In one aspect the invention relates to a method of processing an active ingredient, the method comprising submitting a pharmaceutically active ingredient or ingredients in the absence of excipients (e.g. carrier particles) and/or additives to compression and shearing forces.

In one aspect the invention relates to a method of processing an active ingredient, the method comprising submitting a pharmaceutically active ingredient or ingredients alone to compression and shearing forces.

In one aspect the active is a micronised active.

The invention further relates to an active ingredient obtainable or obtained using the above method.

The invention further relates to an inhaler device comprising an active ingredient obtainable or obtained by the method of the invention, or an active ingredient which has been further processed where necessary into a suitable pharmaceutically acceptable form.

The invention further relates to a receptacle, such as a blister or capsule, comprising a dose of a active ingredient, obtainable or obtained by the method of the invention, or an active ingredient which has been further processed where necessary into a suitable pharmaceutically acceptable form.

BRIEF DESCRIPTION OF THE DRAWINGS/FIGURES

Figure 2:
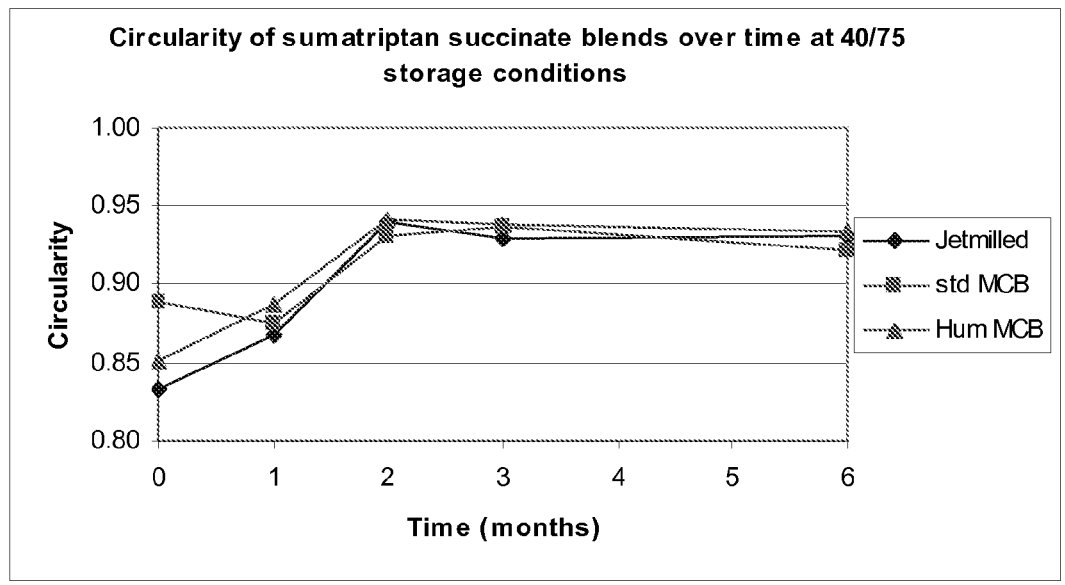
Figure 3:
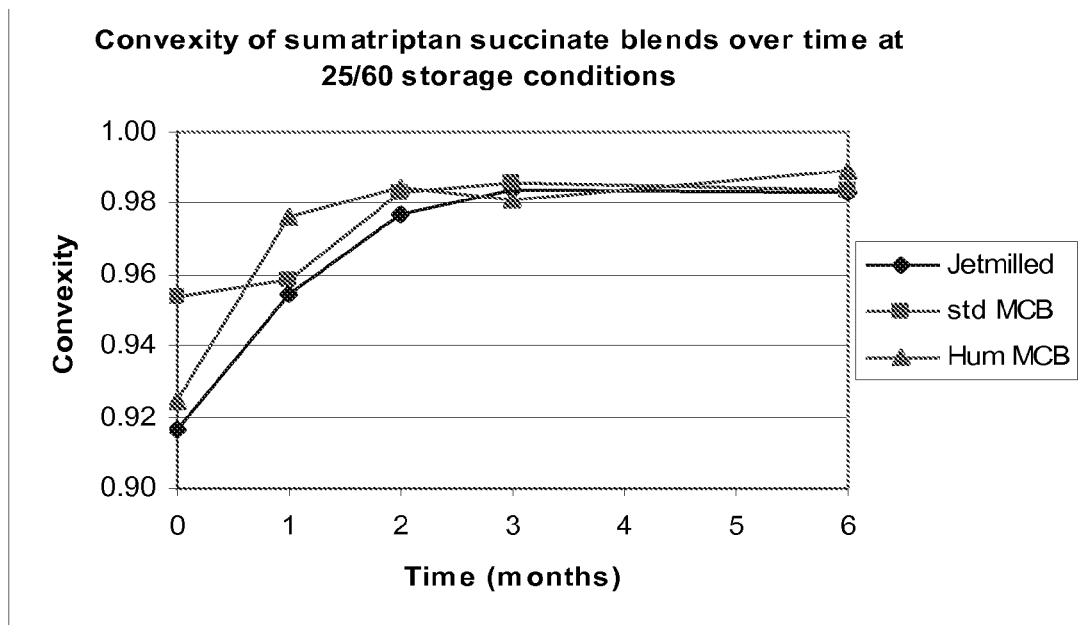
Figure 4:
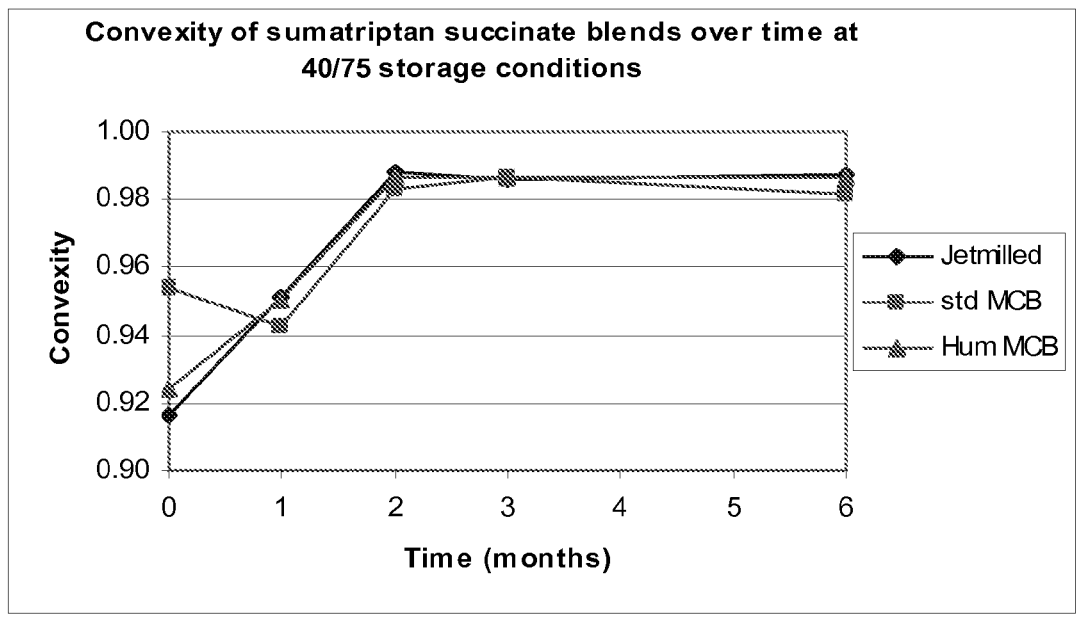
Figure 7:
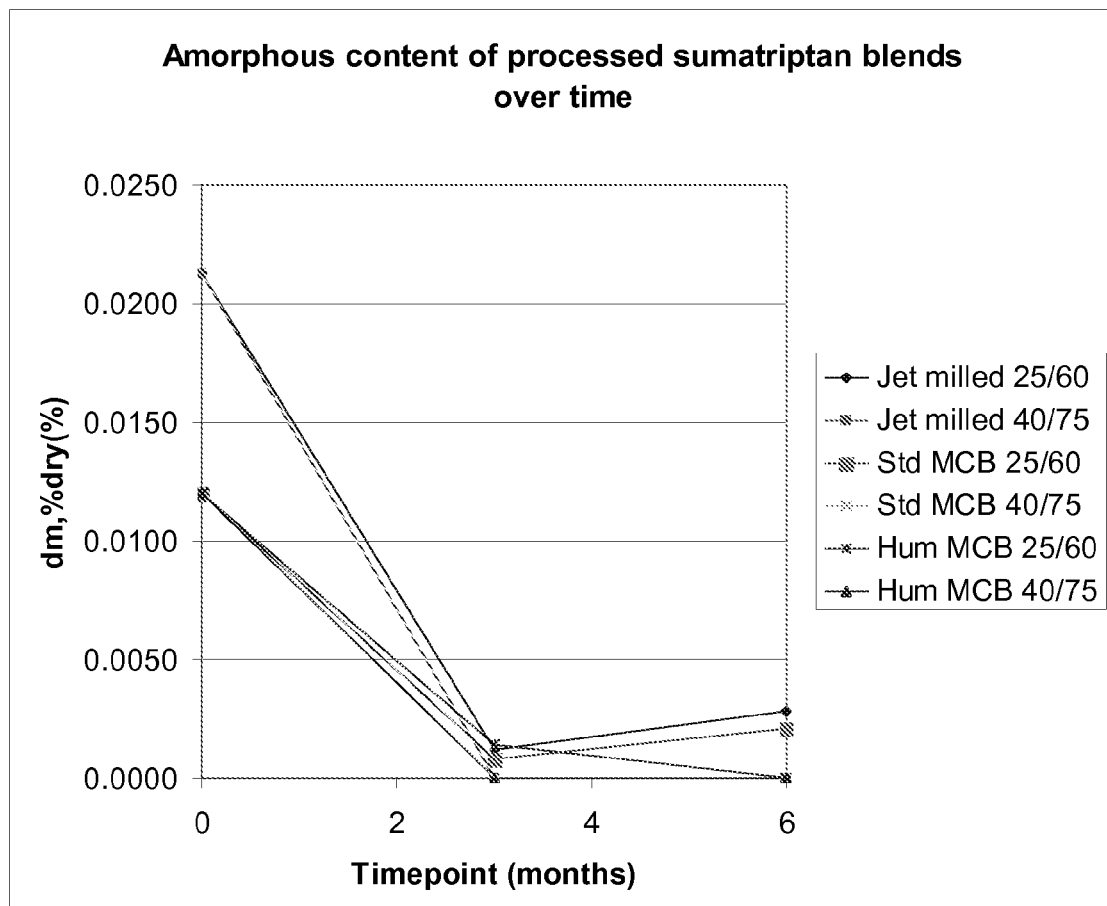
Figure 8:
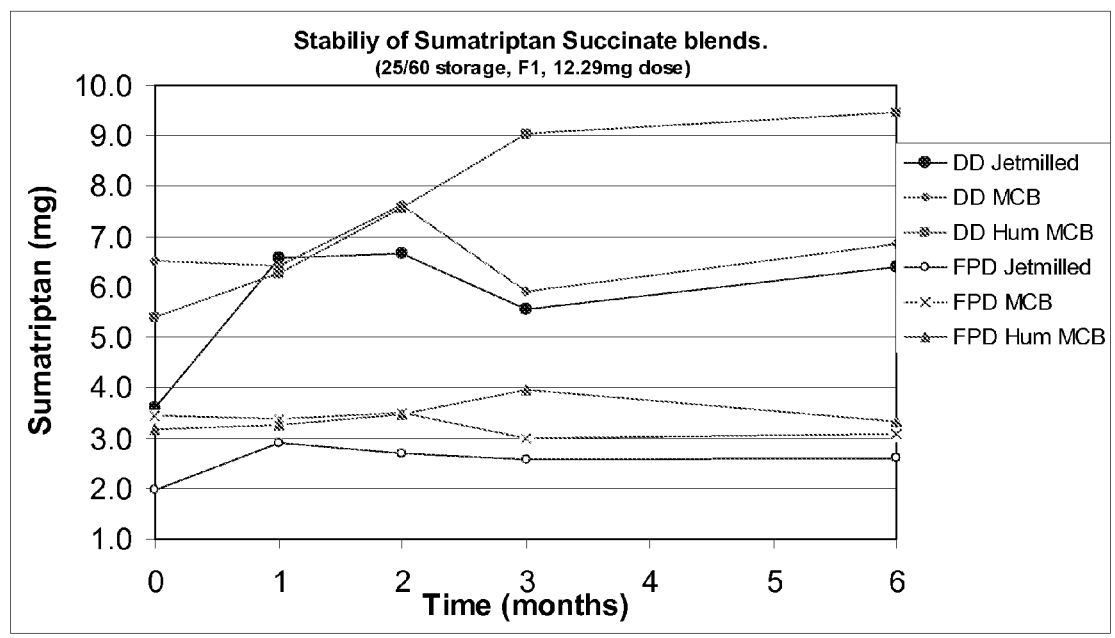
Figure 9:
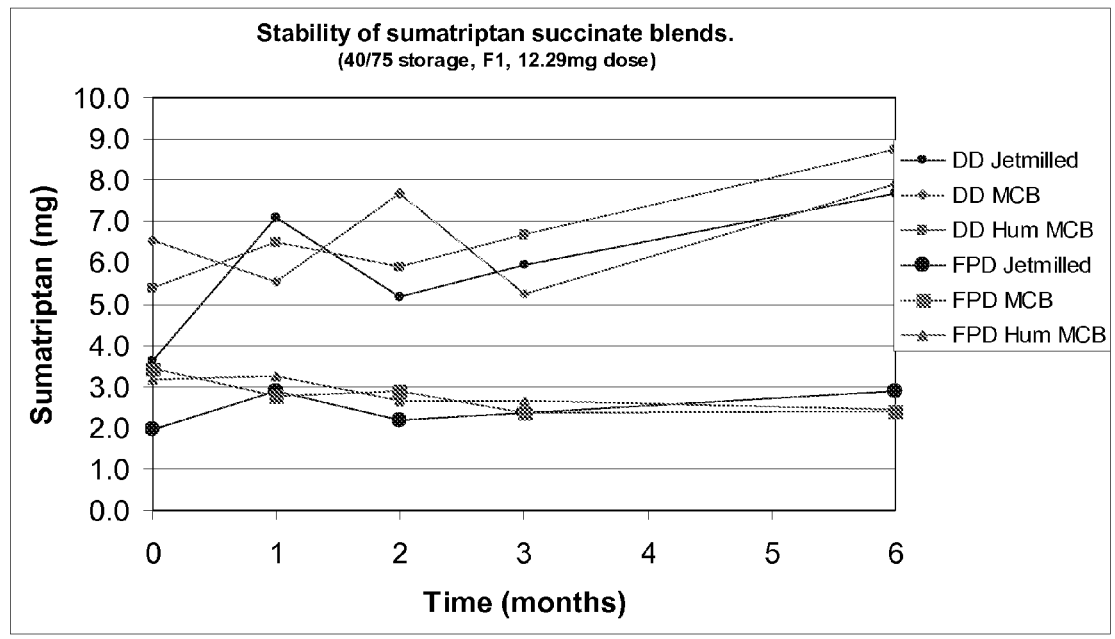

FIG. 1 discloses circularity of sumatriptan succinate over time under different processing conditions and 25/60 storage conditions;

FIG. 2 discloses circularity of sumatriptan succinate over time under different processing conditions and 40/75 storage conditions;

FIG. 3 discloses convexity of sumatriptan succinate over time under different processing conditions and 25/60 storage conditions;

FIG. 4 discloses convexity of sumatriptan succinate over time under different processing conditions and 40/75 storage conditions;

FIG. 5 discloses CE (circle equivalent) diameter of sumatriptan succinate over time under different processing conditions and 25/60 storage conditions;

FIG. 6 discloses CE (circle equivalent) diameter of sumatriptan succinate over time under different processing conditions and 40/75 storage conditions;

FIG. 7 discloses amorphous content of sumatriptan succinate over time after processing (wherein the line describing the Std MCB 25/60 experiment starts between 0.015 and 0.010 dm, is greater than 0.000 at 3 months and the dm rises at 6 months and the line describing the Hum MCB 40/75 experiment starts between 0.015 and 0.010 dm and is 0.000 at 3 months);

FIG. 8 discloses stability of sumatriptan succinate blends under different processing conditions and 25/60 storage conditions, wherein the stability is measured by the delivered and fine particle doses provided via an inhaler device, based upon a nominal dose of 12.29 mg (wherein DD jetmilled starts at 3.6 mg, rises to about 6.6 mg at 1 and 2 months, falls to 5.5 mg at 3 months and rises to 6.4 mg at 6 months; DD MCB starts at over 6.5 mg, falls slightly to 6.4 at 1 month, rises to 7.6 mg at 2 months, falls to 5.9 mg at 3 months and rises to 6.9 mg at 6 months; DD Hum MCB starts at 5.4 mg, rises to 6.3 mg at 1 month, rises further to 7.6 mg at 2 months, rises yet further to 9.1 mg at 3 months and rises yet further to 9.5 mg at 6 months; FPD jetmilled starts at 2 mg, rises to 2.9 mg at 1 month, falls to 2.7 mg at 2 months, falls to 2.6 mg at 3 months and remains the same at 6 months; FPD MCB starts at 3.5 mg, falls to 3.4 mg at 1 month, rises to 3.5 mg at 2 months, falls to 3.0 mg at 3 months and rises to 3.1 mg at 6 months; and FPD Hum MCB starts at 3.2 mg, rises to 3.3 mg at 1 months, rises further to 3.5 at 2 months and further to 3.9 mg at 3 months, before falling to 3.3 mg at 6 months);

FIG. 9 discloses stability of sumatriptan succinate blends under different processing conditions and 40/75 storage conditions, wherein the stability is measured by the delivered and fine particle doses provided via an inhaler device, based upon a nominal dose of 12.29 mg (wherein DD jetmilled starts at 3.6 mg, rises to 7.1 mg at 1 month, falls to 5.2 mg at 2 months, rises to 6.0 mg at 3 months and rises to 7.7 mg at 6 months; DD MCB starts at over 6.5 mg, falls to 5.52 mg at 1 month, rises to 7.7 mg at 2 months, falls to 5.2 mg at 3 months and rises to 7.9 mg at 6 months; DD Hum MCB starts at 5.4 mg, rises to 6.5 mg at 1 month, falls to 5.9 mg at 2 months, rises to 6.7 mg at 3 months and rises yet further to 8.7 mg at 6 months; FPD jetmilled starts at 2 mg, rises to 2.9 mg at 1 month, falls to 2.2 mg at 2 months, rises to 2.4 mg at 3 months and rises to 2.9 mg at 6 months; FPD MCB starts at 3.5 mg, falls to 2.8 mg at 1 month, rises to 2.9 mg at 2 months, falls to just below 2.4 mg at 3 months and rises to 2.4 mg at 6 months; and FPD Hum MCB starts at 3.2 mg, rises to 3.3 mg at 1 months, falls to 2.7 mg at 2 months and maintains this value at 3 months, before falling to 2.4 mg at 6 months).

When used herein, the term "circle equivalent diameter", refers to the diameter of a circle that has the same area as a 2-dimensional image of the particle. Further details of circle equivalent diameter may be found at:

http://www.fei.com/uploadedFiles/Documents/Content/particle_morphology.pdf.

The invention relates, in one aspect, to a method of processing an active ingredient, the method comprising submitting an active ingredient or ingredients alone to compression and shearing forces. Reference to processing of an active ingredient alone herein includes reference to processing of two or more actives alone, unless otherwise clear from the context.

In one aspect, processing of the active ingredient alone indicates that the active is not mixed or coated with any other substance, such as any other solid material, during processing. In one aspect processing of an active alone indicates processing in the absence of other materials that might be suitable for inclusion in a pharmaceutical product. For example, processing is carried out in the absence of an excipient. The invention relates, in one particular aspect, to a method of processing an active ingredient, the method comprising submitting an active ingredient or ingredients alone to compression and shearing forces in the absence of magnesium stearate.

In one aspect the processing of an active alone may be carried out in the presence of a gas or gases that are suitable for, or facilitate or improve the processing step, such as air at room temperature, or at a higher or lower relative humidity than ambient conditions, or gaseous solvents. Gases in this context are not considered to represent a pharmaceutically acceptable material and are not excluded from the processing step.

Without wishing to be bound by theory, subjecting an active agent or agents to compression and shearing forces is thought to reduce the amorphous content of an active ingredient, and may also increase circularity of an active, which properties of the active may lead to improvements in the properties of the particle for inhalation delivery, such as improved stability, flowability and dispersability.

The active ingredient is subjected to a compressive and shearing force.

Suitably the active ingredient is located in a vessel and the force is exerted on the active ingredient between the wall of the vessel and the face of an inner element within the vessel which rotates within the vessel. In one aspect rotation of the inner element results in a compression and shearing force being applied to the active ingredient in the space between the wall and the face of the inner element.

In one aspect a compressive and shearing force is applied in a gap of predetermined width, suitably between the wall of the vessel and an inner element.

In one aspect the compressive and shearing force is achieved by subjecting the active ingredient to mechanofusion (also known as mechanochemical bonding (MCB)), Cyclomix or Hybridiser processes, as described below. In one preferred aspect the compressive and shearing force is achieved by use of mechanofusion technique as described herein.

In one aspect the active ingredient treated in the present invention has a reduced amorphous content, when compared to untreated active ingredient or micronised active ingredient, for example as measured by, Dynamic Vapour Sorption (DVS) analysis as described herein. In one aspect the active ingredient treated in the present invention has reduced amorphous content when compared to the same active ingredient when micronised by jet milling, or when compared to material which has not undergone an MCB step, suitably a reduction of amorphous content of up to 10%, up to 20%, up to 30%, up to 40%, up to 50% or even up to 60%, 70%, 80%, 90% or more, when compared to jet milling, for example as measured by DVS as disclosed herein. In one aspect the amorphous content is not detectable.

In one aspect the active ingredient is in the form of particles prior to processing.

The following processes, which are not limiting, are suitable to provide a compressive and shearing force.

Mechanofusion has previously been described as a dry process designed to mechanically fuse a first material onto a second material. It should be noted that the use of the terms "mechanofusion" and "mechanofused" are supposed to be interpreted as a reference to a particular type of milling process, but not a milling process performed in a particular apparatus. The compressive milling processes work according to a different principle to other milling techniques (Comminution techniques), relying on a particular interaction between an inner element and a vessel wall, and they are based on providing energy by a controlled and substantial compressive force.

The active ingredient is fed into the vessel of a mechano-fusion apparatus (such as a Mechano-Fusion system (Hosokawa Micron Ltd)) or the Nobilta (Hosokawa Micron Ltd) or Nanocular (Hosokawa Micron Ltd) apparatus, where it is subject to a centrifugal force and is pressed against the vessel inner wall. The active ingredient is compressed between the fixed clearance of the drum wall and a curved inner element with high relative speed between drum and element. The inner wall and the curved element together form a gap or nip in which the particles are pressed together. As a result, the active ingredient experiences very high shear forces and very strong compressive stresses as they are trapped between the inner drum wall and the inner element (which has a greater curvature than the inner drum wall). The particles are pressed against each other with enough energy to locally increase the temperature and soften, break, distort, flatten and thereby reduce the amount of amorphous/disordered material in the sample.

Either the outer vessel or the inner element may rotate to provide the relative movement. In an alternate embodiment the outer vessel and the inner element may rotate with respect to each other.

The gap between the outer vessel and the inner element surfaces is relatively small, and is typically less than 10 mm and is preferably less than 5 mm, more preferably less than 3 mm, more preferably less than 2 mm, preferably less than 1 mm or preferably less than 0.5 mm. This gap is fixed, and consequently leads to a better control of the compressive energy than is provided in some other forms of mill such as ball and media mills. Alternatively, a sequential use of rotors with smaller gaps throughout the blending process may be used. Such an approach lends itself to providing control over initial powder processing permitting gentler forces before using rotors with smaller gaps to impart a milling process of greater intensity.

Another compressive milling process that may be used in the present invention is the Cyclomix method. The Cyclomix comprises a stationary conical vessel with a fast rotating shaft with paddles which move close to the wall. Due to the high rotational speed of the paddles, the active ingredient is propelled towards the wall, and as a result it experiences very high shear forces and compressive stresses between wall and paddle. Such effects are similar to those in Mechanofusion as described above and may be sufficient to increase the temperature and soften, to break, distort, and flatten the active ingredient particles.

The device used is preferably capable of exerting a force of greater than 1 N. It will be appreciated by the skilled person, that pressure force that is exerted upon the active will be affected by multiple factors including the force imparted by the rotor on the powder when compressed against the drum wall, the volume of powder within the processing chamber, weight of the powder, density of the powder and the inherent cohesiveness of the powder components which dictate the resistance to flow. In addition to these, the speed, temperature, humidity, amount of powder and type of machine can be varied independently to achieve a suitable form of an active according to the present invention.

In another aspect the compressive and shearing forces may be carried out by the Hybridiser® Method. The active ingredient is fed into the Hybridiser. The powder is subjected to ultra-high speed impact, compression and shear as it is impacted by blades on a high speed rotor inside a stator vessel, and is re-circulated within the vessel. Typical speeds of rotation are in the range of 5,000 to 20,000 rpm.

The above processes suitably apply a high enough degree of force to separate individual particles of active ingredient and to break up tightly bound agglomerates of the active ingredient.

In general, no impaction of milling media surfaces is present so that wear and consequently contamination are minimised.

The speed of rotation may vary between the ranges of 200 to 10,000 rpm through out processing. Typical processing capacity is between 4000-5000 rpm, which equates to 80% engine capacity. It is, however, preferable to introduce powder into the processing chambers at slower speeds. Introduction of powder at slower speeds prevents clogging because it is easier to process an already moving powder. A scraper may also be present to break up any caked material building up on the vessel surface. This is particularly advantageous when using fine cohesive starting materials.

The local temperature may be controlled by use of a heating/cooling jacked built into the drum vessel walls.

The active ingredient may be re-circulated through the vessel.

The pressure and shearing force are exerted for a suitable time to achieve a reduction in the amorphous content of the active ingredient, for example as measured by DVS as disclosed herein. Suitably the time is between 1 minute and 24 hours, such as between 5 minutes and 12 hours, such as between 10 minutes and 2 hours.

Suitably these compression milling processes produce little or no size reduction of the active ingredient, especially where they are already in a micronised form (suitably <10 μm MMAD). One physical change which may be observed is a plastic deformation of the particles to a rounder shape.

The active ingredient may be micronised prior to compression and shearing. Micronisation may be by any suitable method. Micronization is the process of reducing the average diameter of a solid material's particles, for example by milling or grinding. In one aspect a micronised active is an active ingredient that has been subjected to a mechanical process which applies sufficient force to the active ingredient that the process is capable of breaking coarse particles down to fine particles of mass median aerodynamic diameter of not more than 50 μm MMAD as discussed below.

In one aspect micronisation of the active ingredient may be achieved using one or a combination of the following methods: ball milling, jet milling, jet blending, high-pressure homogenation, or any other milling method.

Ball milling is a milling method used in many of the prior art co-milling processes. Centrifugal and planetary ball milling may also be used.

Jet mills are capable of reducing solids to particle sizes in the low-micron to submicron range. The grinding energy is created by gas streams from horizontal grinding air nozzles. Particles in the fluidised bed created by the gas streams are accelerated towards the centre of the mill, colliding within. The gas streams and the particles carried in them create a violent turbulence and, as the particles collide with one another, they are pulverized.

High pressure homogenisers involve a fluid containing the particles being forced through a valve at high pressure, producing conditions of high shear and turbulence. Suitable homogenisers include EmulsiFlex high pressure homogenisers which are capable of pressures up to 4000 bar, Niro Soavi high pressure homogenisers (capable of pressures up to 2000 bar) and Microfluidics Microfluidisers (maximum pressure 2750 bar).

Alternatively micronised active ingredient may be produced by using a high energy media mill or an agitator bead mill, for example, the Netzsch high energy media mill, or the DYNO-mill (Willy A. Bachofen A G, Switzerland).

In one aspect the present invention relates to a method of processing an active ingredient wherein an (optionally micronised) active ingredient is subjected to a compressive and shearing force, in the absence of another powder material.

Various compression methods of the prior art have been used to combine two different powders. Thus the active ingredient of the prior art, such as in EP1498116, is used in combination with materials such as diluting agents, lubricants and coating agents. In contrast the present invention is carried out in the absence of other powders, and thus the effect is obtained on the active ingredient in the absence of powdered excipients, lubricants and coating agents, for example.

In one aspect the processing of the active ingredient is carried out in the absence of any other active ingredient. In one aspect the processing of the active ingredient is carried out in the absence of any excipient. In one aspect the processing of the active ingredient is carried out in the absence of any other lubricant or coating agent.

In a further aspect of the present invention the active ingredient is conditioned during the compression and shearing step.

The term "conditioning" is used herein involves treating the active ingredient by subjecting it to compressive and shearing forces under conditions of controlled relative humidity, temperature, speed of rotation and/or gap width.

In one aspect the active ingredient may be conditioned under conditions of low relative humidity. Preferably, the active is treated under conditions of less than 10% relative humidity.

In one aspect the active ingredient may be conditioned under a humid atmosphere. Preferably, the active ingredient is conditioned under a relative humidity ranging from 5 to 90%. When intending to process under conditions of higher humidity, relative humidity ranges from 50 to 90%, 55 to 87%, 60 to 84%, 65 to 80% and 70 to 75% are preferred. When intending to process under conditions of reduced humidity, ranges are from 5 to 50%, 7.5 to 40%, 10 to 30%, 12.5 to 20% and most preferably less than 15% relative humidity are preferred. In the case of cryogenic preparation, for example liquid nitrogen, reduced humidity ranges will be less than 5%.

The active ingredient may be conditioned under a solvent containing atmosphere, such as an organic solvent. Solvents include alcohols and/or acetone. The skilled artisan would appreciate the nature of risk associated with processing under such environments. Suitable environments include ethanol/nitrogen in ratios of 5:95% (w/w), or more preferably 2.5:97.5% (w/w) or most preferably 1:99% (w/w). Alternatively methanol/nitrogen in ratios of 5:95% (w/w), or more preferably 2.5:97.5% (w/w) or most preferably 1:99% (w/w) may be used. Alternatively acetone/nitrogen in ratios of 5:95% (w/w), or more preferably 2.5:97.5% (w/w) or most preferably 1:99% (w/w) may be used. The solvent may be introduced as a vapour within the gas lines. The solvent may be introduced as a vapour in increasing amounts, from 0%, for example, increasing to 5% (w/w) with processing time. Alternatively, once a steady vapour state is achieved the solvent vapour may be decreased within the vessel with processing time.

Humidity may also be varied over time during the treatment of the active ingredient. The length of time to which the particles are exposed to this humidity may also be varied.

When used herein, "water" is neither an excipient or an additive material.

In another aspect the active ingredient is conditioned at a minimum temperature. Preferably, the temperature is at least 30° C., in one aspect 35° C., in one aspect 40° C., in one aspect 50° C., or higher than 50° C. Processing temperatures may be controlled via an external or integrated cooling jacket. Alternatively, the processing temperature may also be controlled via a suitably heated or cooled atmosphere. Alternatively, temperature may also be varied over time during the treatment of the active ingredient. For example the heated atmosphere may be introduced by increasing temperature with processing time until the desired temperature is achieved. Alternatively, once a steady heated state is achieved the temperature may be decreased within the vessel with processing time.

The particles of the invention may suitably be characterized by their solid state stability. Solid state stability can be assessed using techniques well known in the art. Particular techniques such as DVS may be used. Another method used to characterize the aerosol performance of a powder is by determining the fine particle fraction. The fine particle fraction describes the size distribution of airborne particles. One method of measuring the size distribution, or fine particle fraction, of airborne particles is by impactor testing, for example using a Casacade impactor. One particular technique that may be used is the ACI (Andersen Cascade Impactor). The size cut-off of each stage is dependent on the flow rate at which the ACI is operated.

Atomic force microscopy (AFM) may be used to determine the surface properties of the product either in Surface Topography Analysis or Solid-Solid Interaction Measurements.

Surface Topography Analysis uses a scanning probe method that requires continuous contact between the probing tip and the substrate. Upon encountering protrusions or surface deformations the probe reacts causing a cantilever to bend. This is identified by a laser deflection on the photodiode detector. The varying signal is digitally interpreted and the surface substrate is reconstructed as a 3 dimensional image.

It is also possible to employ an intermittent contact mode, commonly known as Tapping mode, wherein the AFM tip engages with the sample surface thereby reducing the lateral forces which disrupt fragile surfaces. This mode measures a change in amplitude of an oscillating tip. When the tip encounters underlying substrate surfaces, variations in the amplitude of the oscillating tip are recorded by deflection of the laser.

Solid-Solid Interaction Measurements fix a particle of interest on the apex of a cantilever. Under such an arrangement, it is possible to determine the forces between the subject particle and a substrate. By plotting the measured deflection of the cantilever as a function of displacement, a picture of the interaction between the subject particle and substrate can be determined.

The particle morphology may be assessed by a microscope such as Morphologi G3 (Malvern Instruments) which can measure particle circularity and convexity.

The mass median aerodynamic diameter (MMAD) of particles comprising the active ingredient generated using the method of this invention is preferably not more than 10 µm, and advantageously it is not more than 5 µm, more preferably not more than 3 µm and most preferably not more than 1 µm.

Accordingly, advantageously at least 90% by weight of particles comprising the active ingredient have a diameter of not more than 10 µm MMAD, advantageously not more than 5 µm, preferably not more than 3 µm and more preferably not more than 1 µm. In one aspect at least 90% by weight of particles comprising the active ingredient have a mass median aerodynamic diameter in the range of 10 to 2 μm, preferably in the range of 5 to 1 μm, advantageously in the range of 3 to 0.5 μm, and especially advantageously in the range of 2 to 0.05 μm.

Particles comprising the active ingredient may be of a suitable size for inhalation to the desired part of the lung, for example, having an MMAD in the range of 3 to 0.1 μm for absorption in the deep lung, 5 to 0.5 μm for absorption in the respiratory bronchioles, 10 to 2 μm for delivery to the higher respiratory system and 2 to 0.05 μm for delivery to the alveoli.

Additionally, the active particles discussed above may be formulated with excipient particles that have a geometric diameter in the range of 5 to 250 μm, preferably 10 to 100 μm, advantageously 20 to 75 μm, and especially advantageously 40 to 50 μm. The geometric diameter of the particles will not normally be higher than 350 μm.

In one aspect the product of the process of the present invention has a lower amorphous content immediately after treatment when compared to the same material that has been micronized (e.g. impact milled or, more suitably, jet milled).

In one aspect the product of the process of the present invention has a higher delivered dose and/or a higher fine particle dose immediately after treatment when compared to the same material that has been micronized (e.g. impact milled or, more suitably, jet milled).

In one aspect the product of the process of the present invention has a lower surface area, suitably as determined by BET (the BET methodology and theory is discussed in S. Brunauer, P. H. Emmett and E. Teller, *J. Am. Chem. Soc.*, 1938, 60, 309 (BET is derived from the names of the papers authors)) immediately after treatment when compared to the same material that has been micronized (e.g. impact milled or, more suitably, jet milled). "Immediately after treatment" refers to the properties of the product on the day of treatment, suitably as assessed on the day of treatment or very shortly thereafter, in the following one or two days, or held under storage conditions where said properties are essentially maintained.

In one aspect the product of the process of the present invention has a higher circularity or convexity immediately after treatment when compared to the same material that has been micronized (e.g. impact milled or, more suitably, jet milled).

In one aspect the active ingredient produced by the method disclosed herein is stable under 25/60 storage conditions over a six-month (e.g. a five-month, four-month, three-month, two-month or, suitably, one-month) period, wherein the difference in percentage FPF of the nominal dose is no more than ±20% (e.g. ±15%, ±10%, ±7% or, suitably ±5%) of an initial percentage FPF value. For example, when the difference in percentage FPF is no more than ±20%, if the nominal dose is 10 mg and the initial FPF value of the nominal dose is 50% (i.e. a FPD of 5 mg), then the FPF value obtained after six months may not be more than 70% (i.e. more than a FPD of 7 mg) or less than 30% (i.e. less than a FPD of 3 mg) of the nominal dose. The initial percentage FPF value of the nominal dose can be taken immediately after the active ingredient is prepared, but may be taken at any time thereafter and, in this context, reference to the passage of time refers to the amount of time that has elapsed since obtaining the initial percentage FPF value.

When used herein, the terms "25/60 storage conditions" refers to an environment maintained at 25° C. and 60% relative humidity.

When used herein, the terms "40/75 storage conditions" refers to an environment maintained at 40° C. and 75% relative humidity.

The present invention can be carried out with any suitable pharmaceutically active agent. Specific active agents that may be used include, but are not limited to, agents of one or more of the following classes listed below.

1) Adrenergic agonists such as, for example, amphetamine, apraclonidine, bitolterol, clonidine, colterol, dobutamine, dopamine, ephedrine, epinephrine, ethylnorepinephrine, fenoterol, formoterol, guanabenz, guanfacine, hydroxyamphetamine, isoetharine, isoproterenol, isotharine, mephenterine, metaraminol, methamphetamine, methoxamine, methpentermine, methyldopa, methylphenidate, metaproterenol, metaraminol, midodrine, naphazoline, norepinephrine, oxymetazoline, pemoline, phenylephrine, phenylethylamine, phenylpropanolamine, pirbuterol, prenalterol, procaterol, propylhexedrine, pseudo-ephedrine, ritodrine, salbutamol, salmeterol, terbutaline, tetrahydrozoline, tramazoline, tyramine and xylometazoline.
2) Adrenergic antagonists such as, for example, acebutolol, alfuzosin, atenolol, betaxolol, bisoprolol, bopindolol, bucindolol, bunazosin, butyrophenones, carteolol, carvedilol, celiprolol, chlorpromazine, doxazosin, ergot alkaloids, esmolol, haloperidol, indoramin, ketanserin, labetalol, levobunolol, medroxalol, metipranolol, metoprolol, nebivolol, nadolol, naftopidil, oxprenolol, penbutolol, phenothiazines, phenoxybenzamine, phentolamine, pindolol, prazosin, propafenone, propranolol, sotalol, tamsulosin, terazosin, timolol, tolazoline, trimazosin, urapidil and yohimbine.
3) Adrenergic neurone blockers such as, for example, bethanidine, debrisoquine, guabenxan, guanadrel, guanazodine, guanethidine, guanoclor and guanoxan.
4) Drugs for treatment of addiction, such as, for example, buprenorphine.
5) Drugs for treatment of alcoholism, such as, for example, disulfuram, naloxone and naltrexone.
6) Drugs for Alzheimer's disease management, including acetylcholinesterase inhibitors such as, for example, donepezil, galantamine, rivastigmine and tacrin.
7) Anaesthetics such as, for example amethocaine, benzocaine, bupivacaine, hydrocortisone, ketamine, lignocaine, methylprednisolone, prilocaine, proxymetacaine, ropivacaine and tyrothricin.
8) Angiotensin converting enzyme inhibitors such as, for example, captopril, cilazapril, enalapril, fosinopril, imidapril hydrochloride, lisinopril, moexipril hydrochloride, perindopril, quinapril, ramipril and trandolapril.
9) Angiotensin II receptor blockers, such as, for example, candesartan, cilexetil, eprosartan, irbesartan, losartan, medoxomil, olmesartan, telmisartan and valsartan.
10) Antiarrhythmics such as, for example, adenosine, amidodarone, disopyramide, flecamide acetate, lidocaine hydrochloride, mexiletine, procainamide, propafenone and quinidine.
11) Antibiotic and antibacterial agents (including the beta-lactams, fluoroquinolones, ketolides, macrolides, sulphonamides and tetracyclines) such as, for example, aclarubicin, amoxicillin, amphotericin, azithromycin, aztreonam chlorhexidine, clarithromycin, clindamycin, colistimethate, dactinomycin, dirithromycin, doripenem, erythromycin, fusafungine, gentamycin, metronidazole, mupirocin, natamycin, neomycin, nystatin, oleandomycin, pentamidine, pimaricin, probenecid, roxithromycin, sulphadiazine and triclosan.
12) Anti-clotting agents such as, for example, abciximab, acenocoumarol, alteplase, aspirin, bemiparin, bivalirudin, certoparin, clopidogrel, dalteparin, danaparoid, dipyridamole, enoxaparin, epoprostenol, eptifibatide, fondaparin, heparin (including low molecular weight heparin), heparin calcium, lepirudin, phenindione, reteplase, streptokinase, tenecteplase, tinzaparin, tirofiban and warfarin.

13) Anticonvulsants such as, for example, GABA analogs including tiagabine and vigabatrin; barbiturates including pentobarbital; benzodiazepines including alprazolam, chlordiazepoxide, clobazam, clonazepam, diazepam, flurazepam, lorazepam, midazolam, oxazepam and zolazepam; hydantoins including phenyloin; phenyltriazines including lamotrigine; and miscellaneous anticonvulsants including acetazolamide, carbamazepine, ethosuximide, fosphenyloin, gabapentin, levetiracetam, oxcarbazepine, piracetam, pregabalin, primidone, sodium valproate, topiramate, valproic acid and zonisamide.

14) Antidepressants such as, for example, tricyclic and tetracyclic antidepressants including amineptine, amitriptyline (tricyclic and tetracyclic amitryptiline), amoxapine, butriptyline, cianopramine, clomipramine, demexiptiline, desipramine, dibenzepin, dimetacrine, dosulepin, dothiepin, doxepin, imipramine, iprindole, levoprotiline, lofepramine, maprotiline, melitracen, metapramine, mianserin, mirtazapine, nortryptiline, opipramol, propizepine, protriptyline, quinupramine, setiptiline, tianeptine and trimipramine; selective serotonin and noradrenaline reuptake inhibitors (SNRIs) including clovoxamine, duloxetine, milnacipran and venlafaxine; selective serotonin reuptake inhibitors (SSRIs) including citalopram, escitalopram, femoxetine, fluoxetine, fluvoxamine, ifoxetine, milnacipran, nomifensine, oxaprotiline, paroxetine, sertraline, sibutramine, venlafaxine, viqualine and zimeldine; selective noradrenaline reuptake inhibitors (NARIs) including demexiptiline, desipramine, oxaprotiline and reboxetine; noradrenaline and selective serotonin reuptake inhibitors (NASSAs) including mirtazapine; monoamine oxidase inhibitors (MAOIs) including amiflamine, brofaromine, clorgyline, α-ethyltryptamine, etoperidone, iproclozide, iproniazid, isocarboxazid, mebanazine, medifoxamine, moclobemide, nialamide, pargyline, phenelzine, pheniprazine, pirlindole, procarbazine, rasagiline, safrazine, selegiline, toloxatone and tranylcypromine; muscarinic antagonists including benactyzine and dibenzepin; azaspirones including buspirone, gepirone, ipsapirone, tandospirone and tiaspirone; and other antidepressants including acetaphenazine, ademetionine, S-adenosylmethionine, adrafinil, amesergide, amineptine, amperozide, benactyzine, benmoxine, binedaline, bupropion, carbamazepine, caroxazone, cericlamine, cotinine, fezolamine, flupentixol, idazoxan, kitanserin, levoprotiline, lithium salts, maprotiline, medifoxamine, methylphenidate, metralindole, minaprine, nefazodone, nisoxetine, nomifensine, oxaflozane, oxitriptan, phenyhydrazine, rolipram, roxindole, sibutramine, teniloxazine, tianeptine, tofenacin, trazadone, tryptophan, viloxazine and zalospirone.

15) Anticholinergic agents such as, for example, atropine, benzatropine, biperiden, cyclopentolate, glycopyrrolate, hyoscine, ipratropium bromide, orphenadine hydrochloride, oxitroprium bromide, oxybutinin, pirenzepine, procyclidine, propantheline, propiverine, telenzepine, tiotropium, trihexyphenidyl, tropicamide and trospium.

16) Antidiabetic agents such as, for example, pioglitazone, rosiglitazone and troglitazone.

17) Antidotes such as, for example, deferoxamine, edrophonium chloride, fiumazenil, nalmefene, naloxone, and naltrexone.

18) Anti-emetics such as, for example, alizapride, azasetron, benzquinamide, bestahistine, bromopride, buclizine, chlorpromazine, cinnarizine, clebopride, cyclizine, dimenhydrinate, diphenhydramine, diphenidol, domperidone, dolasetron, dronabinol, droperidol, granisetron, hyoscine, lorazepam, metoclopramide, metopimazine, nabilone, ondansetron, palonosetron, perphenazine, prochlorperazine, promethazine, scopolamine, triethylperazine, trifluoperazine, triflupromazine, trimethobenzamide and tropisetron.

19) Antihistamines such as, for example, acrivastine, astemizole, azatadine, azelastine, brompheniramine, carbinoxamine, cetirizine, chlorpheniramine, cinnarizine, clemastine, cyclizine, cyproheptadine, desloratadine, dexmedetomidine, diphenhydramine, doxylamine, fexofenadine, hydroxyzine, ketotifen, levocabastine, loratadine, mizolastine, promethazine, pyrilamine, terfenadine and trimeprazine.

20) Anti-infective agents such as, for example, antivirals (including nucleoside and non-nucleoside reverse transcriptase inhibitors and protease inhibitors) including aciclovir, adefovir, amantadine, cidofovir, efavirenz, famiciclovir, foscarnet, ganciclovir, idoxuridine, indinavir, inosine pranobex, lamivudine, nelfinavir, nevirapine, oseltamivir, palivizumab, penciclovir, pleconaril, ribavirin, rimantadine, ritonavir, ruprintrivir, saquinavir, stavudine, valaciclovir, zalcitabine, zanamivir, zidovudine and interferons; AIDS adjunct agents including dapsone; aminoglycosides including tobramycin; antifungals including amphotericin, caspofungin, clotrimazole, econazole nitrate, fluconazole, itraconazole, ketoconazole, miconazole, nystatin, terbinafine and voriconazole; anti-malarial agents including quinine; antituberculosis agents including capreomycin, ciprofloxacin, ethambutol, meropenem, piperacillin, rifampicin and vancomycin; beta-lactams including cefazolin, cefinetazole, cefoperazone, cefoxitin, cephacetrile, cephalexin, cephaloglycin and cephaloridine; cephalosporins, including cephalosporin C and cephalothin; cephamycins such as cephamycin A, cephamycin B, cephamycin C, cephapirin and cephradine; leprostatics such as clofazimine; penicillins including amoxicillin, ampicillin, amylpenicillin, azidocillin, benzylpenicillin, carbenicillin, carfecillin, carindacillin, clometocillin, cloxacillin, cyclacillin, dicloxacillin, diphenicillin, heptylpenicillin, hetacillin, metampicillin, methicillin, nafcillin, 2-pentenylpenicillin, penicillin N, penicillin O, penicillin S and penicillin V; quinolones including ciprofloxacin, clinafloxacin, difloxacin, grepafloxacin, norfloxacin, ofloxacine and temafloxacin; tetracyclines including doxycycline and oxytetracycline; miscellaneous anti-infectives including linezolide, trimethoprim and sulfamethoxazole.

21) Anti-neoplastic agents such as, for example, droloxifene, tamoxifen and toremifene.

22) Antiparkisonian drugs such as, for example, amantadine, andropinirole, apomorphine, baclofen, benserazide, biperiden, benztropine, bromocriptine, budipine, cabergoline, carbidopa, eliprodil, entacapone, eptastigmine, ergoline, galanthamine, lazabemide, levodopa, lisuride, mazindol, memantine, mofegiline, orphenadrine, trihexyphenidyl, pergolide, piribedil, pramipexole, procyclidine, propentofylline, rasagiline, remacemide, ropinerole, selegiline, spheramine, terguride and tolcapone.

23) Antipsychotics such as, for example, acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine and zuclopenthixol; phenothiazines including aliphatic compounds, piperidines and piperazines; thioxanthenes, butyrophenones and substituted benzamides.

24) Antirheumatic agents such as, for example, diclofenac, heparinoid, hydroxychloroquine and methotrexate, leflunomide and teriflunomide.

25) Anxiolytics such as, for example, adinazolam, alpidem, alprazolam, alseroxlon, amphenidone, azacyclonol, bromazepam, bromisovalum, buspirone, captodiamine, capuride, carbcloral, carbromal, chloral betaine, chlordiazepoxide, clobenzepam, enciprazine, flesinoxan, flurazepam, hydroxyzine, ipsapiraone, lesopitron, loprazolam, lorazepam, loxapine, mecloqualone, medetomidine, methaqualone, methprylon, metomidate, midazolam, oxazepam, propanolol, tandospirone, trazadone, Zolpidem and zopiclone.

26) Appetite stimulants such as, for example, dronabinol.

27) Appetite suppressants such as, for example, fenfluramine, phentermine and sibutramine; and anti-obesity treatments such as, for example, pancreatic lipase inhibitors, serotonin and norepinephrine re-uptake inhibitors, and anti-anorectic agents.

28) Benzodiazepines such as, for example, alprazolam, bromazepam, brotizolam, chlordiazepoxide, clobazam, clonazepam, clorazepate, demoxepam, diazepam, estazolam, flunitrazepam, flurazepam, halazepam, ketazolam, loprazolam, lorazepam, lormetazepam, medazepam, midazolam, nitrazepam, nordazepam, oxazepam, prazepam, quazepam, temazepam and triazolam.

29) Bisphosphonates such as, for example, alendronate sodium, sodium clodronate, etidronate disodium, ibandronic acid, pamidronate disodium, isedronate sodium, tiludronic acid and zoledronic acid.

30) Blood modifiers such as, for example, cilostazol and dipyridamol, and blood factors.

31) Cardiovascular agents such as, for example, acebutalol, adenosine, amiloride, amiodarone, atenolol, benazepril, bisoprolol, bumetanide, candesartan, captopril, clonidine, diltiazem, disopyramide, dofetilide, doxazosin, enalapril, esmolol, ethacrynic acid, flecanide, furosemide, gemfibrozil, ibutilide, irbesartan, labetolol, losartan, lovastatin, metolazone, metoprolol, mexiletine, nadolol, nifedipine, pindolol, prazosin, procainamide, propafenone, propranolol, quinapril, quinidine, ramipril, sotalol, spironolactone, telmisartan, tocamide, torsemide, triamterene, valsartan and verapamil.

32) Calcium channel blockers such as, for example, amlodipine, bepridil, diltiazem, felodipine, flunarizine, gallopamil, isradipine, lacidipine, lercanidipine, nicardipine, nifedipine, nimodipine and verapamil.

33) Central nervous system stimulants such as, for example, amphetamine, brucine, caffeine, dexfenfluramine, dextroamphetamine, ephedrine, fenfluramine, mazindol, methyphenidate, modafmil, pemoline, phentermine and sibutramine.

34) Cholesterol-lowering drugs such as, for example, acipimox, atorvastatin, ciprofibrate, colestipol, colestyramine, bezafibrate, ezetimibe, fenofibrate, fluvastatin, gemfibrozil, ispag hula, nictotinic acid, omega-3 triglycerides, pravastatin, rosuvastatin and simvastatin.

35) Drugs for cystic fibrosis management such as, for example, *Pseudomonas aeruginosa* infection vaccines (eg Aerugen™), alpha 1-anti trip sin, amikacin, cefadroxil, denufosol, duramycin, glutathione, mannitol, and tobramycin.

36) Diagnostic agents such as, for example, adenosine and aminohippuric acid.

37) Dietary supplements such as, for example, melatonin and vitamins including vitamin E.

38) Diuretics such as, for example, amiloride, bendroflumethiazide, bumetanide, chlortalidone, cyclopenthiazide, furosemide, indapamide, metolazone, spironolactone and torasemide.

39) Dopamine agonists such as, for example, amantadine, apomorphine, bromocriptine, cabergoline, lisuride, pergolide, pramipexole and ropinerole.

40) Drugs for treating erectile dysfunction, such as, for example, apomorphine, apomorphine diacetate, moxisylyte, phentolamine, phosphodiesterase type 5 inhibitors, such as sildenafil, tadalafil, vardenafil and yohimbine.

41) Gastrointestinal agents such as, for example, atropine, hyoscyamine, famotidine, lansoprazole, loperamide, omeprazole and rebeprazole.

42) Hormones and analogues such as, for example, cortisone, epinephrine, estradiol, insulin, Ostabolin-C, parathyroid hormone and testosterone.

43) Hormonal drugs such as, for example, desmopressin, lanreotide, leuprolide, octreotide, pegvisomant, protirelin, salcotonin, somatropin, tetracosactide, thyroxine and vasopressin.

44) Hypoglycaemics such as, for example, sulphonylureas including glibenclamide, gliclazide, glimepiride, glipizide and gliquidone; biguanides including metformin; thiazolidinediones including pioglitazone, rosiglitazone, nateglinide, repaglinide and acarbose.

45) Immunoglobulins.

46) Immunomodulators such as, for example, interferon (e.g. interferon beta-Ia and interferon beta-Ib) and glatiramer.

47) Immunosupressives such as, for example, azathioprine, cyclosporin, mycophenolic acid, rapamycin, sirolimus and tacrolimus.

48) Mast cell stabilizers such as, for example, cromoglycate, iodoxamide, nedocromil, ketotifen, tryptase inhibitors and pemirolast.

49) Drugs for treatment of migraine headaches such as, for example, almotriptan, alperopride, amitriptyline, amoxapine, atenolol, clonidine, codeine, coproxamol, cyproheptadine, dextropropoxypene, dihydroergotamine, diltiazem, doxepin, ergotamine, eletriptan, fluoxetine, frovatriptan, isometheptene, lidocaine, lisinopril, lisuride, loxapine, methysergide, metoclopramide, metoprolol, nadolol, naratriptan, nortriptyline, oxycodone, paroxetine, pizotifen, pizotyline, prochlorperazine propanolol, propoxyphene, protriptyline, rizatriptan, sertraline, sumatriptan, timolol, tolfenamic acid, tramadol, verapamil, zolmitriptan, and non-steroidal anti-inflammatory drugs.

50) Drugs for treatment of motion sickness such as, for example, diphenhydramine, promethazine and scopolamine.

51) Mucolytic agents such as N-acetylcysteine, ambroxol, amiloride, dextrans, heparin, desulphated heparin, low molecular weight heparin and recombinant human DNase.

52) Drugs for multiple sclerosis management such as, for example, bencyclane, methylprednisolone, mitoxantrone and prednisolone.

53) Muscle relaxants such as, for example, baclofen, chlorzoxazone, cyclobenzaprine, methocarbamol, orphenadrine, quinine and tizanidine.
54) NMDA receptor antagonists such as, for example, memantine.
55) Nonsteroidal anti-inflammatory agents such as, for example, aceclofenac, acetaminophen, alminoprofen, amfenac, aminopropylon, amixetrine, aspirin, benoxaprofen, bromfenac, bufexamac, carprofen, celecoxib, choline, cinchophen, cinmetacin, clometacin, clopriac, diclofenac, diclofenac sodium, diflunisal, ethenzamide, etodolac, etoricoxib, fenoprofen, flurbiprofen, ibuprofen, indomethacin, indoprofen, ketoprofen, ketorolac, loxoprofen, mazipredone, meclofenamate, mefenamic acid, meloxicam, nabumetone, naproxen, nimesulide, parecoxib, phenylbutazone, piroxicam, pirprofen, rofecoxib, salicylate, sulindac, tiaprofenic acid, tolfenamate, tolmetin and valdecoxib.
56) Nucleic-acid medicines such as, for example, oligonucleotides, decoy nucleotides, antisense nucleotides and other gene-based medicine molecules.
57) Opiates and opioids such as, for example, alfentanil, allylprodine, alphaprodine, anileridine, benzylmorphine, bezitramide, buprenorphine, butorphanol, carbiphene, cipramadol, clonitazene, codeine, codeine phosphate, dextromoramide, dextropropoxyphene, diamorphine, dihydrocodeine, dihydromorphine, diphenoxylate, dipipanone, fentanyl, hydromorphone, L-alpha acetyl methadol, levorphanol, lofentanil, loperamide, meperidine, meptazinol, methadone, metopon, morphine, nalbuphine, nalorphine, oxycodone, papaveretum, pentazocine, pethidine, phenazocine, pholcodeine, remifentanil, sufentanil, tramadol, and combinations thereof with an anti-emetic.
58) Opthalmic preparations such as, for example, betaxolol and ketotifen.
59) Osteoporosis preparations such as, for example, alendronate, estradiol, estropitate, raloxifene and risedronate.
60) Other analgesics such as, for example, apazone, benzpiperylon, benzydamine, caffeine, cannabinoids, clonixin, ethoheptazine, flupirtine, nefopam, orphenadrine, pentazocine, propacetamol and propoxyphene.
61) Other anti-inflammatory agents such as, for example, B-cell inhibitors, p38 MAP kinase inhibitors and TNF inhibitors.
62) Phosphodiesterase inhibitors such as, for example, non-specific phosphodiesterase inhibitors including theophylline, theobromine, IBMX, pentoxifylline and papaverine; phosphodiesterase type 3 inhibitors including bipyridines such as milrinone, aminone and olprinone; imidazolones such as piroximone and enoximone; imidazolines such as imazodan and 5-methyl-imazodan; imidazo-quinoxalines; and dihydropyridazinones such as indolidan and LYI 81512 (5-(6-oxo-I, 4,5, 6-tetrahydro-pyridazin-3-yl)-1,3-dihydro-indol-2-one); dihydroquinolinone compounds such as cilostamide, cilostazol, and vesnarinone; motapizone; phosphodiesterase type 4 inhibitors such as cilomilast, etazolate, rolipram, oglemilast, roflumilast, ONO 6126, tolafentrine and zardaverine, and including quinazolinediones such as nitraquazone and nitraquazone analogs; xanthine derivatives such as denbufylline and arofylline; tetrahydropyrimidones such as atizoram; and oxime carbamates such as filaminast; and phosphodiesterase type 5 inhibitors including sildenafil, zaprinast, vardenafil, tadalafil, dipyridamole, and the compounds described in WO 01/19802, particularly (S)-2-(2-hydroxymethyl-1-pyrrolidinyl)-4-(3-chloro-4-methoxy-benzylamino)-5-[N-(2-pyrimidinylmethyl)carbamoyl]pyrimidine, 2-(5,6,7,8-tetrahydro-1,7-naphthyridin-7-yl)-4-(3-chloro-4-methoxybenzylamino)-5-[N-(2-morpholinoethyl) carbamoyl]-pyrimidine, and (S)-2-(2-hydroxymethyl-1-pyrrolidinyl)-4-(3-chloro-4-methoxy-benzylamino)-5-[N-(1,3,5-trimethyl-4-pyrazolyl)carbamoyl]-pyrimidine).
63) Potassium channel modulators such as, for example, cromakalim, diazoxide, glibenclamide, levcromakalim, minoxidil, nicorandil and pinacidil.
64) Prostaglandins such as, for example, alprostadil, dinoprostone, epoprostanol and misoprostol.
65) Respiratory agents and agents for the treatment of respiratory diseases including bronchodilators such as, for example, the β2-agonists bambuterol, bitolterol, broxaterol, carmoterol, clenbuterol, fenoterol, formoterol, indacaterol, levalbuterol, metaproterenol, orciprenaline, picumeterol, pirbuterol, procaterol, reproterol, rimiterol, salbutamol, salmeterol, terbutaline and the like; inducible nitric oxide synthase (iNOS) inhibitors; the antimuscarinics ipratropium, ipratropium bromide, oxitropium, tiotropium, glycopyrrolate and the like; the xanthines aminophylline, theophylline and the like; adenosine receptor antagonists, cytokines such as, for example, interleukins and interferons; cytokine antagonists and chemokine antagonists including cytokine synthesis inhibitors, endothelin receptor antagonists, elastase inhibitors, integrin inhibitors, leukotriene receptor antagonists, prostacyclin analogues, and ablukast, ephedrine, epinephrine, fenleuton, iloprost, iralukast, isoetharine, isoproterenol, montelukast, ontazolast, pranlukast, pseudoephedrine, sibenadet, tepoxalin, verlukast, zafirlukast and zileuton.
66) Sedatives and hypnotics such as, for example, alprazolam, butalbital, chlordiazepoxide, diazepam, estazolam, flunitrazepam, flurazepam, lorazepam, midazolam, temazepam, triazolam, zaleplon, Zolpidem, and zopiclone.
67) Serotonin agonists such as, for example, I-(4-bromo-2,5-dimethoxyphenyl)-2-aminopropane, buspirone, m-chlorophenylpiperazine, cisapride, ergot alkaloids, gepirone, 8-hydroxy-(2-N,N-dipropylamino)-tetraline, ipsaperone, lysergic acid diethylamide, 2-methyl serotonin, mezacopride, sumatriptan, tiaspirone, trazodone and zacopride.
68) Serotonin antagonists such as, for example, amitryptiline, azatadine, chlorpromazine, clozapine, cyproheptadine, dexfenfluramine, R(+)-α-(2,3-dimethoxyphenyl)-I-[2-(4-fluorophenyl)ethyl]-4-piperidine-methanol, dolasetron, fenclonine, fenfluramine, granisetron, ketanserin, methysergide, metoclopramide, mianserin, ondansetron, risperidone, ritanserin, trimethobenzamide and tropisetron.
69) Steroid drugs such as, for example, alcometasone, beclomethasone, beclomethasone dipropionate, betamethasone, budesonide, butixocort, ciclesonide, clobetasol, deflazacort, diflucortolone, desoxymethasone, dexamethasone, fludrocortisone, flunisolide, fluocinolone, fluometholone, fluticasone, fluticasone proprionate, hydrocortisone, methylprednisolone, mometasone, nandrolone decanoate, neomycin sulphate, prednisolone, rimexolone, rofleponide, triamcinolone and triamcinolone acetonide.
70) Sympathomimetic drugs such as, for example, adrenaline, dexamfetamine, dipirefin, dobutamine, dopamine, dopamine, isoprenaline, noradrenaline, phenylephrine, pseudoephedrine, tramazoline and xylometazoline.
71) Nitrates such as, for example, glyceryl trinitrate, isosorbide dinitrate and isosorbide mononitrate.
72) Skin and mucous membrane agents such as, for example, bergapten, isotretinoin and methoxsalen.
73) Smoking cessation aids such as, for example, bupropion, nicotine and varenicline.

74) Drugs for treatment of Tourette's syndrome such as, for example, pimozide.
75) Drugs for treatment of urinary tract infections such as, for example, darifenicin, oxybutynin, propantheline bromide and tolteridine.
76) Vaccines (e.g. solid vaccines).
77) Drugs for treating vertigo such as, for example, betahistine and meclizine.
78) Therapeutic proteins and peptides such as acylated insulin, glucagon, glucagon-like peptides, exendins, insulin, insulin analogues, insulin aspart, insulin detemir, insulin glargine, insulin glulisine, insulin lispro, insulin zinc, isophane insulins, neutral, regular and insoluble insulins, and protamine zinc insulin. Suitable proteins are solid proteins.
79) Anticancer agents such as, for example, anthracyclines, doxorubicin, idarubicin, epirubicin, methotrexate, taxanes, paclitaxel, docetaxel, cisplatin, vinca alkaloids, vincristine and 5-fluorouracil.
80) Pharmaceutically acceptable salts or derivatives of any of the foregoing.

In addition, the active ingredient used in the present invention may be small molecules, proteins, carbohydrates or mixtures thereof.

It should be noted that drugs listed above under a particular indication or class may also find utility in other indications. A plurality of active agents can be employed in the practice of the present invention. Active ingredients made in the present invention may be combined with other active ingredients, optionally also be made by processes of the present invention, suitably to form a drug for inhalation.

Specific combinations of two medicaments which may be mentioned include combinations of steroids and β2-agonists. Examples of such combinations are beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and formoterol; ciclesonide and salmeterol; mometasone and formoterol; and mometasone and salmeterol. Other combinations include β2-agonists and antimuscarinics, as well as the combination of steroid, LAMA (long-acting muscarinic antagonist) and LABA (Long-acting beta2-agonist), such as a steroid, tiotropium (LAMA) and formoterol (LABA).

In one aspect, APIs for use in the invention are able to be micronised by impact milling or, more suitably, by jet milling.

The skilled person will also appreciate those physical parameters, such as indentation hardness, will assist in the identification of those actives (also called active pharmaceutical ingredients or APIs herein) suitable for working according to the teachings of the invention. Furthermore, the skilled person would understand what processes are required to modify unsuitable APIs in order to make them suitable for working according to the invention. For example, Vickers hardness test, Brinell hardness test, Knoop hardness test, Meyer hardness test, Rockwell hardness test, Shore durometer hardness or the Barcol hardness test, may be used to assess the suitability of the target API. Those APIs initially found unsuitable for working according to the present invention, may be, for example, cryogenically treated prior to or during working.

In one embodiment of the present invention, there is provided an active ingredient obtainable or obtained using any of the methods described in the specification, suitably in the form of a powder such as a dry powder, the latter suitably containing less than 10%, more preferably less than 7% or most preferably less that 5% (w/w) water or other fluid.

In a further embodiment of the present invention there is provided a composition, preferably a pharmaceutical composition, comprising an active ingredient made by a method according to the present invention in combination with an additional ingredient such as an additive, carrier and/or flavouring agent or other excipient.

In one aspect the additive material is an anti-adherent material that will tend to decrease the cohesion between the active ingredient, and between the active ingredient and other particles present in the pharmaceutical composition.

The additive material may be an anti-friction agent (glidant), suitably to give better flow of the pharmaceutical composition in, for example, a dry powder inhaler which will lead to a better dose reproducibility.

Where reference is made to an anti-adherent material, or to an anti-friction agent, the reference is to include those materials which are able to decrease the cohesion between the particles, or which will tend to improve the flow of powder in an inhaler, even though they may not usually be referred to as anti-adherent material or an anti-friction agent. For example, leucine is an anti-adherent material as herein defined and is generally thought of as an anti-adherent material but lecithin is also an anti-adherent material as herein defined, even though it is not generally thought of as being anti-adherent, because it will tend to decrease the cohesion between the active ingredient and between the active ingredient and other particles present in the pharmaceutical composition.

The additive material may be in the form of particles which tend to adhere to the surfaces of active ingredient, as disclosed in WO1997/03649. Alternatively, the additive material may be coated on the surface of the active ingredient by a co-milling method, as disclosed in WO 2002/43701. Therefore, in one aspect of the invention, the method may further comprise and additional step of coating the surface of the active ingredient with an additive material (e.g. by a co-milling method).

The additive material may include one or more compounds selected from amino acids and derivatives thereof, and peptides and derivatives thereof. Amino acids, peptides and derivatives of peptides are suitably physiologically acceptable and give acceptable release of the active ingredient on inhalation.

The additive may comprise one or more of any of the following amino acids: leucine, isoleucine, lysine, valine, methionine, and phenylalanine. The additive may be a salt or a derivative of an amino acid, for example aspartame or acesulfame K. Preferably, the additive consists substantially of an amino acid, more preferably of leucine, advantageously L-leucine. The L-, D- and DL-forms of an amino acid may also be used. As indicated above, leucine has been found to give particularly efficient dispersal of the active ingredient on inhalation.

The additive may include one or more water soluble substances. A water soluble substance may be a substance that may be capable of dissolving wholly or partly in water and which is not entirely insoluble in water. This may help absorption of the additive by the body if it reaches the lower lung. The additive may include dipolar ions, which may be zwitterions. It is also advantageous to include a spreading agent as an additive, to assist with the dispersal of the composition in the lungs. Suitable spreading agents include surfactants such as known lung surfactants (e.g. ALEC™) which comprise phospholipids, for example, mixtures of DPPC (dipalmitoyl phosphatidylcholine) and PG (phosphatidylglycerol). Other suitable surfactants include, for example, dipalmitoyl phosphatidyl than olamine (DPPE), dipalmitoyl phosphatidylinositol (DPPI).

The additive may comprise a metal stearate, or a derivative thereof, for example, sodium stearyl fumarate or sodium stearyl lactylate. Advantageously, it comprises a metal stearate, for example, zinc stearate, magnesium stearate, calcium stearate, sodium stearate or lithium stearate. Preferably, the additive material comprises magnesium stearate, for example vegetable magnesium stearate, or any form of commercially available metal stearate, which may be of vegetable or animal origin and may also contain other fatty acid components such as palmitates or oleates.

The additive may include or consist of one or more surface active materials. A surface active material may be a substance capable reducing the surface tension of a liquid in which it is dissolved. Surface active materials may in particular be materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific examples of such materials are phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina HR; and sugar esters in general. Alternatively, the additive may be cholesterol.

Other possible additive materials include sodium benzoate, hydrogenated oils which are solid at room temperature, talc, titanium dioxide, aluminium dioxide, silicon dioxide and starch. Also useful as additives are film-forming agents, fatty acids and their derivatives, as well as lipids and lipid-like materials.

In one aspect additive particles are composed of lactose. The additive particles may be lactose fines. The additive lactose may be added a various stages of the formulation assembly or the additive lactose may be formed as a result of processing of a larger lactose carrier particle. Said processing produces smaller lactose particles that may adhere to the larger carrier particles or combine with different components of the composition.

In one aspect a plurality of different additive materials can be used.

Carrier particles may be of any acceptable inert excipient material or combination of materials. For example, carrier particles frequently used in the prior art may be composed of one or more materials selected from sugar alcohols, polyols and crystalline sugars. Other suitable carriers include inorganic salts such as sodium chloride and calcium carbonate, organic salts such as sodium lactate and other organic compounds such as polysaccharides and oligosaccharides. Advantageously, the carrier particles comprise a polyol. In particular, the carrier particles may be particles of crystalline sugar, for example mannitol, dextrose or lactose. Preferably, the carrier particles are composed of lactose. Suitable examples of such excipient include LactoHale 300 (Friesland Foods Domo), LactoHale 200 (Friesland Foods Domo), LactoHale 100 (Friesland Foods Domo), PrismaLac 40 (Meggle), InhaLac 70 (Meggle).

The ratio in which the carrier particles (if present) and active ingredient are mixed will depend on the type of inhaler device used, the type of active particle used and the required dose. The carrier particles may be present in an amount of at least 50%, more preferably 70%, advantageously 90% and most preferably 95% based on the combined weight of the active ingredient and the carrier particle.

The invention also relates to a method of processing an active ingredient, the method comprising submitting micronised active ingredients or, more suitably, a micronised active ingredient to compression and shearing forces in the absence of a powder material and then combining the active ingredients or, more suitably, active ingredient with another agent, such as another active ingredient, an excipient or additive.

The invention further relates to a method of processing an active ingredient, the method comprising submitting micronised active ingredients or, more suitably, a micronised active ingredient alone to compression and shearing forces and then combining the active ingredients or, more suitably, active ingredient with another agent, such as another active ingredient, an excipient or additive.

The invention provides an active ingredient for use in a pharmaceutical composition, preferably a pharmaceutical composition for inhalation, more preferably a powder for a dry powder inhaler. Preferably, the active ingredient may be for use in a pharmaceutical composition for a pressurized metered dose inhaler (pMDI).

The invention further provides an active ingredient obtained by the method of the present invention for use in medicine, and use of an active ingredient obtained by the method of the present invention in the preparation of a medicament for prevention or treatment of disease, for example, including diseases approved for treatment with known active ingredients listed above.

In another embodiment of the present invention, powders in accordance with the present invention may be administered using active or passive devices.

In one embodiment of the invention, the inhaler device is an active device, in which a source of compressed gas or alternative energy source is used. Examples of suitable active devices include Aspirair™ (Vectura), Microdose™ and the active inhaler device produced by Nektar Therapeutics (as covered by U.S. Pat. No. 6,257,233).

In an alternative embodiment, the inhaler device is a passive device, in which the patient's breath is the only source of gas which provides a motive force in the device. Examples of "passive" dry powder inhaler devices include the Rotahaler™ and Diskhaler™ (GlaxoSmithKline) and the Turbohaler™ (Astra-Draco), Monohaler™ (Miat), GyroHaler™ (Vectura) and Novolizer™ (Viatris GmbH).

The size of the doses can vary from micrograms to milligrams, depending upon the active ingredient, the delivery device and disease to be treated. Suitably the dose will range from 1 ng to 50 mg of active ingredient, more preferably 10 µg to 20 mg being preferred and most preferably 100 µg to 10 mg being more preferred. The skilled artisan will appreciate that dose of the active will depend on the nature of the active pharmaceutical ingredient, therefore a dose of 1 mg to 10 mg, more preferably 2 mg to 8 mg, more preferably 3 mg to 7 mg and most preferably 4 mg to 5 mg is required. Alternatively a dose of 5 mg to 15 mg, more preferably 6 mg to 14 mg, more preferably 7 mg to 13 mg and most preferably 8 mg to 12 mg is required. Alternatively a dose of 10 mg to 20 mg, more preferably 12 mg to 18 mg, more preferably 14 mg to 16 mg and most preferably 14.5 mg to 15.5 mg is required. Alternatively a dose of 20 mg to 25 mg, more preferably 21 mg to 24 mg, more preferably 22 mg to 23 mg and most preferably 22.5 mg is required. Doses referred to above are nominal doses.

Reference to doses herein is generally a reference to metered doses (MD) (or nominal doses (ND), the two terms may be used interchangeably). The MD is the dose of active pharmaceutical ingredient in the blister or capsule or formulation holding receptacle.

The emitted dose (ED) or delivered dose (DD) (the two terms may be used interchangeably) is the total mass of the active agent emitted from the device following actuation. It does not include the material left on the internal or external surfaces of the device, or in the metering system including, for example, the capsule or blister. The ED is measured by collecting the total emitted mass from the device in an apparatus frequently identified as a dose uniformity sampling apparatus (DUSA), and recovering this by a validated quantitative wet chemical assay (a gravimetric method is possible, but this is less precise).

The fine particle dose (FPD) is the total mass of active agent which is emitted from the device following actuation which is present in an aerodynamic particle size smaller than a defined limit. This limit is generally taken to be 5 μm MMAD if not expressly stated to be an alternative limit, such as 3 μm, 2 μm or 1 μm, etc.

The fine particle fraction (FPF) is normally defined as the FPD (the dose that is <5 μm MMAD) divided by the delivered Dose (DD) which is the dose that leaves the device. The FPF is expressed as a percentage. Herein, the FPF of DD is referred to as FPF (DD) and is calculated as FPF (DD)=(FPD/DD)×100%.

The fine particle fraction (FPF) may also be defined as the FPD divided by the Metered Dose (MD) which is the dose in the blister or capsule, and expressed as a percentage. Herein, the FPF of MD is referred to as FPF (MD), and may be calculated as FPF (MD)=(FPD/MD)×100%.

According to an embodiment of the present invention, a receptacle is provided, holding a dose of the active ingredient prepared according to the present invention. The receptacle may be a capsule or blister, preferably a foil blister.

Active ingredient, suitably in the form of a powder, in accordance with the present invention may be pre-metered. The powders may be kept in foil blisters which offer chemical and physical protection whilst not being detrimental to the overall performance. Indeed, the formulations thus packaged tend to be stable over long periods of time, which is very beneficial, especially from a commercial and economic point of view.

In one embodiment, the composition according to the present invention is held in a receptacle containing a single dose of the powder, the contents of which may be dispensed using one of the aforementioned devices.

Reservoir devices may also be used.

The invention also relates to a method of processing an active ingredient, the method comprising submitting an active ingredient to compression and shearing forces in the absence of another powder material, optionally then combining the active ingredient with another agent, such as another active ingredient, an excipient or additive, and then packaging the active ingredient into a receptacle or drug delivery device.

In one aspect the invention relates to a method of processing an ingredient for use in a pharmaceutical composition, the method comprising submitting the ingredient to compression and shearing forces in the absence of another powder material.

In the embodiments discussed above, the ingredient is an active agent, such as a drug, capable of having a prophylactic or therapeutic effect. However, alternatively, the ingredient is a pharmaceutically acceptable component other than an active, for example, an excipient such as an additive, carrier and/or flavouring agents and/or taste masking agent as described above, which then may optionally be used in combination with an active to provide a pharmaceutical composition.

The above disclosure made in relation to the processing of active ingredients applies equally to a method for processing other pharmaceutically acceptable ingredients, such as excipients, and to pharmaceutical compositions comprising the ingredient, delivery devices comprising the ingredient and packaged doses of the pharmaceutical composition comprising the ingredient, unless otherwise apparent from the context, and references to processing of active may be replaced with references to processing of other pharmaceutically acceptable ingredients, as appropriate.

The ingredient may be combined with other components of a pharmaceutical composition, such as an active ingredient or excipient. In one aspect such other components may also have been subjected to compression and shearing forces in the absence of another powder material.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the measurement, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is illustrated by the by the experimental data set out below, which is not limiting upon the invention:

EXAMPLES

In the experiments, the active ingredient used was sumatriptan succinate. Different treatments of the active were compared for different physical properties, as listed below:

Example 1.1

Jet Milled Sumatriptan Succinate

This example studied the disordered/amorphous content of jet milled Sumatriptan Succinate.
Methods Jet Milling, of blend CSS090120RPA, was carried out using AS 50 spiral jet mill (Hosokawa), sumatriptan succinate (Natco), feed rate (first pass) 3.2 g/min, feed rate (second pass) 4 g/min, compressed air supply, venturi 5 bar, grind 3 bar, on a 100 g batch size.

Convexity, (number distribution), circularity (number distribution) and circular equivalent diameter (number distribution) were measured by Morphologi G3 optical microscope on a dry dispersion of 1 mm$^3$ of material using 25 μm foil. The parameters were 4 bar injection pressure, injection time 10 ms, settling time 120 seconds. X20 magnification. Trash size 10 pixels. Approx 5000 particles measured.

DVS, sample size approximately 100 mg. The sample was then analysed using a Surface Measurement Systems DVS1 with the following programme: % RH: 0, 20, 40, 50, 60, 70, 80, 90—two symmetrical cycles at 40° C. with a set step time of 90 minutes.

ACI, Device (F1), Blister 17.2 mg fill weight (nominal dose of sumatriptan=12.29 mg). Flow rate and time adjusted to achieve a 4 kPa pressure drop and 4 liters of air (in the region of 60 l/min and 4 seconds).

Surface area, BET by Beckman Coulter SA3100 Gas Adsorption Apparatus—3-10 hr outgas at 60° C. max. BET profile. 60° C. max during analysis. Sample size 160 mg-860 mg.

The results of analysis is listed below:
Convexity, (table 1)
Circularity, (table 1)
DVS, (table 2 & 3)
ACI, (table 2)
Surface area, (table 4)
Particle Size, (table 1)

Example 1.2

Jet Milled Sumatriptan Succinate which is Processed by MCB

Methodology

Jet Milling, Convexity, Circularity, DVS, ACI, Surface area, Particle Size and circular equivalent diameter, were all carried out as in example 1.1 The same jet milled batch as example 1.1 was used.

MCB processing was carried out using blend CSS090121RPA and a Hosokawa minikit, 1 mm rotor gap, 20 g batch size, Powder processing: 5 minutes @ 5% speed (powder addition), 5 mins @ 20% speed, stepped up to 80% speed (10% increments) for 10 minutes. Closed loop chilling unit 19° C. setpoint.
Results
Convexity, (table 1)
Circularity, (table 1)
DVS, (table 2 & 3)
ACI, (table 2)
Surface area, (table 4)
Particle Size, (table 1)

Example 1.3

Jet Milled and MCB Processed Sumatriptan Succinate with Elevated Humidity

Jet Milling, Convexity, Circularity, DVS, ACI, Surface area, Particle Size, circular equivalent diameter, were carried out as in example 1. The same Jet milled batch as example 1.1 was used.

MCB processing was carried out on blend CSS090121KCA, Hosokawa minikit, 1 mm rotor gap, 20 g batch size, elevated humidity supplied by humidifying an external chamber and transferred via tubing, solenoid and pump (2 l/min), humidity measured by thermohygrometer=81.6% RH. Powder processing: 5 minutes @ 5% speed (powder addition), 5 mins @ 20% speed, stepped up to 80% speed (10% increments) for 10 minutes. Closed loop chilling unit setpoint 19° C.
Results
Convexity, (table 1)
Circularity, (table 1)
DVS, (table 2 & 3)
ACI, (table 2)
Surface area, (table 4)
Particle Size, (table 1)

Example 1.4

Jet Milled and MCB Processed Sumatriptan Succinate with Reduced Humidity

Jet Milling, blend CSS080828RPA, was carried out using AS 50 spiral jet mill (Hosokawa), sumatriptan succinate (Natco), feed rate (first pass) 3 g/min, feed rate (second pass) 3 g/min, compressed air supply, venturi 5 bar, grind 3 bar. 80 g batch size.

MCB processing was carried out on blend CSS080829RPA, using a Hosokawa minikit, 1 mm rotor gap, 20 g batch size, reduced humidity supplied by compressed air via tubing, solenoid and pump (2 l/min), humidity measured by thermohygrometer=LT 10% RH. Powder processing: 5 minutes @ 5% speed (powder addition), 5 mins @ 20% speed, stepped up to 80% speed (10% increments) for 10 minutes. Mains water cooled at 19° C.

DVS and ACI analysis was carried out according to Example 1.1.

Particle Size was assessed using a Malvern Mastersizer 200, with a dry cell dispersion.
Results
DVS, see (table 2)
ACI, see (table 2)
Surface area, 4.28 m$^2$/g
Particle Size, d0.1 μm=0.761, d0.5 μm=1.787, d0.9 μm=3.692

TABLES

TABLE 1

Morphologi G3 data table - circularity, convexity and particle size for: i) jet milled sumatriptan succinate. ii) jet milled and MCB processed sumatriptan succinate in ambient conditions. iii) jet milled and MCB processed in raised humidity.

| Time point | Conditions | Sample | Replicate | Convexity Mean | Combined convexity mean (of 3 reps) | Circularity mean | Combined circularity mean (of 3 reps) | CE diameter D(0.1) μm | Mean CE diameter D(0.1) μm | CE diameter D(0.5) μm | Mean CE diameter D(0.5) μm | CE diameter D(0.9) μm | Mean CE diameter D(0.9) μm |
|---|---|---|---|---|---|---|---|---|---|---|---|---|---|
| Initial (T = 0) | n/a | Jet milled | 1 | 0.915 | 0.916 | 0.832 | 0.832 | 1.56 | 1.57 | 2.92 | 2.86 | 4.88 | 4.80 |
| | | CSS09012 | 2 | 0.914 | | 0.829 | | 1.63 | | 2.89 | | 4.75 | |
| | | 0RPA | 3 | 0.920 | | 0.836 | | 1.52 | | 2.78 | | 4.78 | |
| | | Std MCB | 1 | 0.949 | 0.954 | 0.883 | 0.888 | 1.52 | 1.49 | 2.70 | 2.79 | 4.48 | 4.81 |
| | | CSS09012 | 2 | 0.956 | | 0.890 | | 1.49 | | 2.87 | | 5.19 | |
| | | 1RPA | 3 | 0.956 | | 0.892 | | 1.47 | | 2.79 | | 4.77 | |
| | | Hum MCB | 1 | 0.953 | 0.924 | 0.889 | 0.851 | 1.50 | 1.48 | 2.85 | 3.15 | 4.65 | 4.98 |
| | | CSS09012 | 2 | 0.904 | | 0.828 | | 1.82 | | 3.36 | | 5.20 | |
| | | 1KCA | 3 | 0.916 | | 0.835 | | 1.13 | | 3.23 | | 5.08 | |
| T = 1 month | 25/60 | Jet milled | 1 | 0.961 | 0.954 | 0.890 | 0.882 | 1.05 | 1.15 | 2.19 | 2.23 | 4.33 | 4.17 |
| | | CSS09012 | 2 | 0.949 | | 0.875 | | 1.25 | | 2.26 | | 4.07 | |
| | | 0RPA | 3 | 0.953 | | 0.880 | | 1.14 | | 2.23 | | 4.12 | |
| | | Std MCB | 1 | 0.973 | 0.959 | 0.920 | 0.901 | 1.46 | 1.60 | 2.64 | 2.77 | 4.52 | 4.57 |
| | | CSS09012 | 2 | 0.973 | | 0.920 | | 1.45 | | 2.62 | | 4.46 | |
| | | 1RPA | 3 | 0.930 | | 0.862 | | 1.89 | | 3.06 | | 4.74 | |
| | | Hum MCB | 1 | 0.976 | 0.976 | 0.926 | 0.925 | 1.46 | 1.34 | 2.66 | 2.61 | 4.63 | 4.59 |
| | | CSS09012 | 2 | 0.976 | | 0.925 | | 1.50 | | 2.70 | | 4.73 | |
| | | 1KCA | 3 | 0.977 | | 0.923 | | 1.05 | | 2.47 | | 4.41 | |
| | 40/75 | Jet milled | 1 | 0.958 | 0.951 | 0.876 | 0.868 | 0.81 | 0.97 | 2.22 | 2.39 | 4.53 | 4.53 |
| | | CSS09012 | 2 | 0.946 | | 0.869 | | 1.18 | | 2.60 | | 4.55 | |
| | | 0RPA | 3 | 0.949 | | 0.860 | | 0.93 | | 2.36 | | 4.52 | |
| | | Std MCB | 1 | 0.931 | 0.943 | 0.861 | 0.875 | 2.07 | 1.84 | 3.54 | 3.41 | 5.68 | 5.85 |
| | | CSS09012 | 2 | 0.952 | | 0.887 | | 1.79 | | 3.35 | | 6.02 | |
| | | 1RPA | 3 | 0.945 | | 0.876 | | 1.65 | | 3.35 | | 5.86 | |
| | | Hum MCB | 1 | 0.953 | 0.951 | 0.892 | 0.887 | 1.77 | 1.69 | 3.11 | 3.09 | 5.26 | 5.14 |
| | | CSS09012 | 2 | 0.956 | | 0.890 | | 1.49 | | 3.03 | | 5.09 | |
| | | 1KCA | 3 | 0.943 | | 0.878 | | 1.82 | | 3.13 | | 5.07 | |
| T = 2 month | 25/60 | Jet milled | 1 | 0.971 | 0.977 | 0.897 | 0.909 | 0.82 | 0.84 | 1.79 | 1.76 | 3.61 | 3.78 |
| | | CSS09012 | 2 | 0.974 | | 0.900 | | 0.75 | | 1.63 | | 3.81 | |
| | | 0RPA | 3 | 0.985 | | 0.931 | | 0.94 | | 1.86 | | 3.93 | |
| | | Std MCB | 1 | 0.986 | 0.983 | 0.939 | 0.933 | 1.25 | 1.29 | 2.31 | 2.36 | 4.19 | 4.21 |
| | | CSS09012 | 2 | 0.979 | | 0.926 | | 1.34 | | 2.42 | | 4.31 | |
| | | 1RPA | 3 | 0.984 | | 0.935 | | 1.27 | | 2.34 | | 4.14 | |
| | | Hum MCB | 1 | 0.979 | 0.985 | 0.927 | 0.939 | 1.28 | 1.24 | 2.44 | 2.34 | 4.13 | 4.12 |
| | | CSS09012 | 2 | 0.987 | | 0.944 | | 1.22 | | 2.30 | | 4.19 | |
| | | 1KCA | 3 | 0.988 | | 0.945 | | 1.22 | | 2.27 | | 4.04 | |
| | 40/75 | Jet milled | 1 | 0.990 | 0.988 | 0.943 | 0.939 | 0.92 | 0.95 | 1.77 | 1.79 | 3.61 | 3.62 |
| | | CSS09012 | 2 | 0.986 | | 0.935 | | 0.96 | | 1.80 | | 3.66 | |
| | | 0RPA | 3 | 0.988 | | 0.940 | | 0.96 | | 1.79 | | 3.58 | |
| | | Std MCB | 1 | 0.983 | 0.983 | 0.936 | 0.931 | 1.14 | 1.15 | 2.45 | 2.53 | 4.62 | 4.80 |
| | | CSS09012 | 2 | 0.981 | | 0.925 | | 1.20 | | 2.61 | | 5.01 | |
| | | 1RPA | 3 | 0.985 | | 0.931 | | 1.11 | | 2.54 | | 4.78 | |
| | | Hum MCB | 1 | 0.987 | 0.986 | 0.944 | 0.942 | 1.24 | 1.27 | 2.34 | 2.39 | 4.07 | 4.15 |
| | | CSS09012 | 2 | 0.984 | | 0.937 | | 1.31 | | 2.48 | | 4.28 | |
| | | 1KCA | 3 | 0.988 | | 0.945 | | 1.27 | | 2.34 | | 4.09 | |
| T = 3 month | 25/60 | Jet milled | 1 | 0.988 | 0.984 | 0.940 | 0.927 | 0.91 | 0.96 | 1.85 | 2.01 | 4.34 | 4.51 |
| | | CSS09012 | 2 | 0.983 | | 0.925 | | 0.98 | | 2.06 | | 4.54 | |
| | | 0RPA | 3 | 0.980 | | 0.916 | | 1.00 | | 2.11 | | 4.65 | |
| | | Std MCB | 1 | 0.989 | 0.986 | 0.941 | 0.935 | 1.12 | 1.12 | 2.13 | 2.16 | 3.90 | 4.04 |
| | | CSS09012 | 2 | 0.981 | | 0.924 | | 1.13 | | 2.20 | | 4.02 | |
| | | 1RPA | 3 | 0.988 | | 0.940 | | 1.12 | | 2.14 | | 4.19 | |
| | | Hum MCB | 1 | 0.982 | 0.981 | 0.926 | 0.924 | 1.23 | 1.21 | 2.46 | 2.43 | 4.42 | 4.33 |
| | | CSS09012 | 2 | 0.980 | | 0.923 | | 1.20 | | 2.43 | | 4.26 | |
| | | 1KCA | 3 | 0.980 | | 0.923 | | 1.21 | | 2.40 | | 4.32 | |
| | 40/75 | Jet milled | 1 | 0.986 | 0.986 | 0.929 | 0.929 | 0.98 | 1.00 | 2.16 | 2.08 | 4.65 | 4.39 |
| | | CSS09012 | 2 | 0.984 | | 0.925 | | 1.03 | | 2.07 | | 4.42 | |
| | | 0RPA | 3 | 0.988 | | 0.934 | | 0.98 | | 2.00 | | 4.11 | |
| | | Std MCB | 1 | 0.986 | 0.987 | 0.934 | 0.936 | 1.13 | 1.13 | 2.24 | 2.24 | 4.21 | 4.20 |
| | | CSS09012 | 2 | 0.988 | | 0.940 | | 1.14 | | 2.24 | | 4.26 | |
| | | 1RPA | 3 | 0.986 | | 0.935 | | 1.12 | | 2.23 | | 4.13 | |
| | | Hum MCB | 1 | 0.988 | 0.987 | 0.940 | 0.939 | 1.18 | 1.20 | 2.38 | 2.36 | 4.43 | 4.31 |
| | | CSS09012 | 2 | 0.983 | | 0.930 | | 1.25 | | 2.48 | | 4.51 | |
| | | 1KCA | 3 | 0.989 | | 0.947 | | 1.18 | | 2.23 | | 3.98 | |
| T = 6 month | 25/60 | Jet milled | 1 | 0.986 | 0.983 | 0.924 | 0.918 | 0.88 | 0.94 | 1.93 | 2.05 | 4.09 | 4.22 |
| | | CSS09012 | 2 | 0.978 | | 0.904 | | 0.97 | | 2.13 | | 4.31 | |
| | | 0RPA | 3 | 0.984 | | 0.926 | | 0.96 | | 2.09 | | 4.25 | |
| | | Std MCB | 1 | 0.987 | 0.984 | 0.934 | 0.926 | 0.97 | 1.02 | 1.98 | 2.14 | 3.99 | 4.26 |
| | | CSS09012 | 2 | 0.979 | | 0.916 | | 1.15 | | 2.35 | | 4.76 | |
| | | 1RPA | 3 | 0.986 | | 0.929 | | 0.93 | | 2.09 | | 4.04 | |
| | | Hum MCB | 1 | 0.991 | 0.989 | 0.945 | 0.940 | 0.97 | 1.02 | 1.85 | 1.94 | 3.40 | 3.55 |

TABLE 1-continued

Morphologi G3 data table - circularity, convexity and particle size for: i) jet milled sumatriptan succinate. ii) jet milled and MCB processed sumatriptan succinate in ambient conditions. iii) jet milled and MCB processed in raised humidity.

| Time point | Conditions | Sample | Replicate | Convexity Mean | Combined convexity mean (of 3 reps) | Circularity mean | Combined circularity mean (of 3 reps) | CE diameter D(0.1) μm | Mean CE diameter D(0.1) μm | CE diameter D(0.5) μm | Mean CE diameter D(0.5) μm | CE diameter D(0.9) μm | Mean CE diameter D(0.9) μm |
|---|---|---|---|---|---|---|---|---|---|---|---|---|---|
| | | CSS09012 | 2 | 0.986 | | 0.934 | | 1.09 | | 2.04 | | 3.69 | |
| | | 1KCA | 3 | 0.990 | | 0.942 | | 1.01 | | 1.93 | | 3.56 | |
| 40/75 | | Jet milled | 1 | 0.988 | 0.987 | 0.935 | 0.931 | 0.99 | 0.94 | 1.97 | 1.91 | 3.92 | 3.92 |
| | | CSS09012 | 2 | 0.987 | | 0.931 | | 0.94 | | 1.87 | | 3.94 | |
| | | 0RPA | 3 | 0.986 | | 0.926 | | 0.88 | | 1.90 | | 3.90 | |
| | | Std MCB | 1 | 0.977 | 0.982 | 0.911 | 0.922 | 1.00 | 1.05 | 2.35 | 2.26 | 4.61 | 4.44 |
| | | CSS09012 | 2 | 0.985 | | 0.930 | | 1.20 | | 2.34 | | 4.60 | |
| | | 1RPA | 3 | 0.983 | | 0.924 | | 0.94 | | 2.09 | | 4.10 | |
| | | Hum MCB | 1 | 0.983 | 0.986 | 0.928 | 0.934 | 1.11 | 1.10 | 2.18 | 2.14 | 4.13 | 4.03 |
| | | CSS09012 | 2 | 0.987 | | 0.935 | | 1.13 | | 2.17 | | 4.09 | |
| | | 1KCA | 3 | 0.989 | | 0.938 | | 1.06 | | 2.08 | | 3.88 | |

TABLE 2

ACI and DVS results for: i) jet milled sumatriptan succinate. Ii) jet milled and MCB processed sumatriptan succinate in ambient conditions. Iii) jet milled and MCB processed in raised humidity. Iii) jet milled and MCB processed in reduced humidity.

| | 25/60 | | | | | 40/75 | | | | |
|---|---|---|---|---|---|---|---|---|---|---|
| | DD (mg) | FPD (mg) | FPF (%) | FPF as % of nominal | Amorphous phase content dm, % dry (%) | DD (mg) | FPD (mg) | FPF (%) | FPF as % of nominal | Amorphous phase content dm, % dry (%) |
| JetMilled | | | | | | | | | | |
| 0 | 3.60 | 1.97 | 55.3 | 16.0 | 0.0213 | 3.60 | 1.97 | 55.3 | 16.0 | 0.0213 |
| 1 | 6.57 | 2.90 | 44.4 | 23.6 | n/a | 7.07 | 2.86 | 40.4 | 23.3 | n/a |
| 2 | 6.67 | 2.68 | 40.9 | 21.8 | n/a | 5.17 | 2.16 | 41.3 | 17.6 | n/a |
| 3 | 5.54 | 2.58 | 46.70 | 21.0 | 0.0012 | 5.95 | 2.37 | 40.30 | 19.30 | ND |
| 6 | 6.40 | 2.61 | 41.20 | 21.2 | 0.0028 | 7.68 | 2.87 | 37.8 | 23.4 | ND |
| Std MCB | | | | | | | | | | |
| 0 | 6.52 | 3.45 | 53.6 | 28.1 | 0.0120 | 6.52 | 3.45 | 53.6 | 28.1 | 0.012 |
| 1 | 6.41 | 3.37 | 52.8 | 27.4 | n/a | 5.52 | 2.78 | 50.8 | 22.6 | n/a |
| 2 | 7.62 | 3.51 | 46.1 | 28.6 | n/a | 7.66 | 2.89 | 38.1 | 23.5 | n/a |
| 3 | 5.90 | 3.00 | 50.7 | 24.4 | 0.0008 | 5.23 | 2.35 | 45.00 | 19.10 | ND |
| 6 | 6.85 | 3.07 | 45.7 | 25.0 | 0.0021 | 7.90 | 2.40 | 30.40 | 19.50 | ND |
| Humid MCB | | | | | | | | | | |
| 0 | 5.39 | 3.16 | 60.0 | 25.7 | 0.0120 | 5.39 | 3.16 | 60.0 | 25.7 | 0.012 |
| 1 | 6.26 | 3.26 | 52.6 | 26.5 | n/a | 6.51 | 3.25 | 51.1 | 26.4 | n/a |
| 2 | 7.57 | 3.46 | 45.9 | 28.2 | n/a | 5.89 | 2.66 | 45.8 | 21.6 | n/a |
| 3 | 9.05 | 3.94 | 44.0 | 32.1 | 0.0014 | 6.68 | 2.66 | 40.13 | 21.60 | ND |
| 6 | 9.46 | 3.33 | 35.2 | 27.1 | ND | 8.73 | 2.43 | 27.90 | 19.80 | ND |

| Reduced Humidity MCB | Prototype F1 device | | | | Amorphous phase |
|---|---|---|---|---|---|
| | DD (mg) | FPD (mg) | FPF (%) | FPF as % of nominal | content dm, % dry (%) |
| 0 | 7.29 | 3.92 | 53.77 | 31.90 | 0.0121 | n/a = test not performed.
ND = amorphous phase Not Detected.

TABLE 3

ACI and DVS results for: i) jet milled sumatriptan succinate. ii) jet milled and MCB processed sumatriptan succinate in ambient conditions. iii) jet milled and MCB processed in raised humidity.

| | | Mass Loss (%) | | |
|---|---|---|---|---|
| Process | Condition | Initial | 3 months | 6 months |
| Jet mill | 25° C./60% RH | 0.0213 | 0.0012 | 0.0028 |
| Jet mill | 40° C./75% RH | | ND | ND |
| Jet mill, MCB | 25° C./60% RH | 0.0120 | 0.0008 | 0.0021 |
| Jet mill, MCB | 40° C./75% RH | | ND | ND |
| Jet mill, humid MCB | 25° C./60% RH | 0.0120 | 0.0014 | ND |
| Jet mill, humid MCB | 40° C./75% RH | | ND | ND |

TABLE 4

BET surface area measurements for: i) jet milled sumatriptan succinate. ii) jet milled and MCB processed sumatriptan succinate in ambient conditions. iii) jet milled and MCB processed sumatriptan succinate in raised humidity.

| Blend BN | Sample description | T = 0 BET surface area m$^2$/g | T = 6 months @ 25/60 BET surface area m$^2$/g | T = 6 months @ 40/75 BET surface area m$^2$/g |
|---|---|---|---|---|
| CSS090120RPA | Sumatriptan succinate jetmilled | 4.736 | 3.944 | 3.380 |
| CSS090121RPA | Sumatriptan succinate MCB processed | 3.735 | 3.311 | 2.880 |
| CSS090121KCA | Sumatriptan succinate humid MCB processed | n/a | 3.237 | 2.421 |

CONCLUSIONS

Examples 1-4

DVS analysis points to the formation of surface disordered (amorphous) structure as a result of jet milling technique. The amorphous content of the same starting material when processed by a process involving compression and shearing, under both humid (82% RH) and dry (10% RH) conditions, results in a product with less amorphous product after processing than jet milling. That product demonstrated higher levels of delivered dose and fine particle fraction, inter alia, than a jet milled product. The product of the invention produced by compression and shearing forces has a greater circularity and convexity after treatment than the same jet milled product. The product of the invention produced by compression and shearing forces has a less variable profile from T=0 months to T=1 month, in a period where profile of the jet milled product is highly variable, for example, as assessed by delivered dose. Thus the process of the present invention provides an active with enhanced properties in comparison with a jet milled product.

Further, as shown by Table 3, the variability of the FPF (when based upon nominal dose) is less for the mechanofused active ingredient compared to the active ingredient that has undergone jetmilling only.

What is claimed:

1. A method of processing an active ingredient, the method consisting of feeding a pharmaceutically active ingredient to a mechanofusion apparatus and subjecting the pharmaceutically active ingredient to compression and shearing forces, wherein the active ingredient is micronized prior to compression and shearing forces and wherein the active ingredient is glycopyrrolate.

2. The method of claim 1, wherein the active is conditioned during compression and shearing.

3. The method of claim 2, wherein the active is conditioned by an elevated level of relative humidity compared to ambient conditions.

4. The method of claim 3, wherein the active is conditioned by increasing the relative humidity over time to 70%.

5. The method of claim 1, wherein the active ingredient is conditioned at a minimum temperature.

6. The method of claim 2, wherein the active ingredient is conditioned at a minimum temperature.

7. The method of claim 3, wherein the active ingredient is conditioned at a minimum temperature.

8. The method of claim 4, wherein the active ingredient is conditioned at a minimum temperature.

9. The method of claim 5, wherein the minimum temperature is at least 50° C.

10. The method of claim 6, wherein the minimum temperature is at least 50° C.

11. The method of claim 7, wherein the minimum temperature is at least 50° C.

12. The method of claim 8, wherein the minimum temperature is at least 50° C.

13. The method of claim 1, wherein the micronization is impact milling or jet milling.

14. The method of claim 13, wherein an amorphous content of the active is reduced with respect to the micronised active starting material, suitably as measured by DVS.

15. A method of processing an active ingredient according to claim 1, wherein the active material is combined after compression and shearing with another material, wherein the another material is selected from a group consisting of another active, carrier and additive; or further processed.

16. A method according to claim 1, wherein the active ingredient is packaged after processing into a receptacle or delivery device.

* * * * *